(12) United States Patent
Raduchel

(10) Patent No.: US 9,619,616 B2
(45) Date of Patent: Apr. 11, 2017

(54) RECORDS ACCESS AND MANAGEMENT

(71) Applicant: eIngot LLC, Great Falls, VA (US)

(72) Inventor: William J. Raduchel, Great Falls, VA (US)

(73) Assignee: eIngot LLC, Great Falls, VA (US)

( * ) Notice: Subject to any disclaimer, the term of this patent is extended or adjusted under 35 U.S.C. 154(b) by 113 days.

(21) Appl. No.: 14/523,110

(22) Filed: Oct. 24, 2014

(65) Prior Publication Data

US 2015/0046192 A1    Feb. 12, 2015

Related U.S. Application Data

(63) Continuation-in-part of application No. 14/083,691, filed on Nov. 19, 2013, which is a continuation of application No. 12/167,746, filed on Jul. 3, 2008, now Pat. No. 8,600,776.

(60) Provisional application No. 60/974,997, filed on Sep. 25, 2007, provisional application No. 60/947,809, filed on Jul. 3, 2007.

(51) Int. Cl.
| | |
|---|---|
| *G06Q 50/00* | (2012.01) |
| *G06F 19/00* | (2011.01) |
| *H04W 8/18* | (2009.01) |
| *H04W 12/06* | (2009.01) |
| *G06Q 50/24* | (2012.01) |
| *G06Q 10/06* | (2012.01) |

(52) U.S. Cl.
CPC .......... *G06F 19/323* (2013.01); *G06F 19/322* (2013.01); *G06Q 10/063* (2013.01); *G06Q 50/24* (2013.01); *H04W 8/18* (2013.01); *H04W 12/06* (2013.01)

(58) Field of Classification Search
CPC .............................. G06F 19/323; H04W 8/18
See application file for complete search history.

(56) References Cited

U.S. PATENT DOCUMENTS

| | | |
|---|---|---|
| 5,995,943 A | 11/1999 | Bull et al. |
| 6,463,417 B1 | 10/2002 | Schoenberg |
| 6,988,075 B1 | 1/2006 | Hacker |
| 7,466,235 B1 | 12/2008 | Kolb et al. |
| 8,600,776 B2 | 12/2013 | Raduchel |
| 2002/0010679 A1 | 1/2002 | Felsher |

(Continued)

FOREIGN PATENT DOCUMENTS

CN    1650305    8/2005

OTHER PUBLICATIONS

International Search Report and Written Opinion in International Application No. PCT/US15/56961, mailed Jan. 11, 2016, 12 pages.

(Continued)

*Primary Examiner* — Phil Nguyen
(74) *Attorney, Agent, or Firm* — Fish & Richardson P.C.

(57) ABSTRACT

An electronic device for aggregating electronic medical records, in which electronic medical records are aggregated from multiple electronic repositories and displayed as a single set of records. The multiple electronic repositories may store records for a particular patient using varying identifying/access information to facilitate anonymous access to the electronic medical records. Emergency medical services providers may be able to access medical records for a patient using the electronic device after being authenticated as a valid/licensed medical services provider.

47 Claims, 14 Drawing Sheets

(56) References Cited

U.S. PATENT DOCUMENTS

| | | | |
|---|---|---|---|
| 2002/0016821 A1* | 2/2002 | Son | G06F 19/321 709/204 |
| 2002/0042884 A1 | 4/2002 | Wu et al. | |
| 2003/0140044 A1* | 7/2003 | Mok | G06Q 50/22 |
| 2003/0233342 A1 | 12/2003 | Vadrot | |
| 2004/0260577 A1* | 12/2004 | Dahlin | G06Q 50/22 705/2 |
| 2007/0027721 A1 | 2/2007 | Hasan et al. | |
| 2007/0061170 A1 | 3/2007 | Lorsch | |
| 2007/0078677 A1 | 4/2007 | Hofstetter | |
| 2008/0109651 A1 | 5/2008 | Duda et al. | |
| 2009/0012817 A1 | 1/2009 | Squires et al. | |
| 2009/0037224 A1 | 2/2009 | Raduchel | |
| 2012/0078660 A1 | 3/2012 | Mangicaro et al. | |
| 2014/0081669 A1 | 3/2014 | Raduchel | |

OTHER PUBLICATIONS

U.S. Final Office action for U.S. Appl. No. 14/083,691 on Mar. 24, 2016, 16 pages.

Roseberry, Can Any Bluetooth Enabled Cell Phone Be Used as a Modem?, Jul. 23, 2006, /mobileoffice.about.com/od/usingyourphone/f/bluetoothphones.htm>.

Chinese Notification of the First Office Action (with English translation) for Application No. 200880022802.5 dated May 24, 2011, 9 pages.

PCT Notification of Transmittal of the International Search Report and the Written Opinion for Application No. PCT/US08/69228 dated Sep. 10, 2008, 15 pages.

PCT Notification Concerning Transmittal of International Preliminary Report on Patentability for Application No. PCT/US2008/069228 dated Jan. 5, 2010, 11 pages.

Office Action issued in CN201210112416.3 on Sep. 22, 2014, with English Translation, 20 pages.

U.S. Non-Final Office Action for U.S. Appl. No. 12/167,746 dated Oct. 12, 2010, 12 pages.

U.S. Final Office Action for U.S. Appl. No. 12/167,746 dated May 5, 2011, 10 pages.

U.S. Notice of Allowance for U.S. Appl. No. 12/167,746 dated Jul. 29, 2013, 13 pages.

U.S. Non-Final Office Action for U.S. Appl. No. 14/083,691 dated Mar. 27, 2014, 13 pages.

U.S. Non-Final Office Action for U.S. Appl. No. 14/083,691 dated Oct. 23, 2014, 16 pages.

U.S. Final Office Action for U.S. Appl. No. 14/083,691 dated Mar. 30, 2015, 12 pages.

U.S. Non-Final Office Action for U.S. Appl. No. 14/083,691 dated Jul. 17, 2015, 10 pages.

U.S. Notice of Allowance for U.S. Appl. No. 14/083,691, dated Jun. 17, 2016, 11 pages.

* cited by examiner

RECORDS ACCESS AND MANAGEMENT

CROSS-REFERENCE TO RELATED APPLICATIONS

This application is a continuation in part of (and claims the benefit of priority under 35 USC 120) of U.S. application Ser. No. 14/083,691, filed Nov. 19, 2013, which is a continuation of U.S. application Ser. No. 12/167,746, filed Jul. 3, 2008, now allowed, which claims priority from U.S. Provisional Application No. 60/947,809, filed on Jul. 3, 2007, and entitled "Records Access and Management," and also claims priority from U.S. Provisional Application No. 60/974,997, filed on Sep. 25, 2007, and entitled "Records Access and Management." The entire content of the prior applications is incorporated herein by reference in its entirety.

FIELD

The present disclosure generally relates to records access and management.

BACKGROUND

Medical records may be stored by specific medical service providers in paper or electronic formats. When medical records need to be transferred or gathered from multiple medical service providers, the transfer and gathering may be difficult and time consuming.

SUMMARY

In one general sense, techniques and systems are described for aggregating medical records for a user. A process of aggregating electronic medical records associated with a patient is initiated, the process being initiated in response to the patient providing user input to an electronic device associated with the patient. A first request for one or more electronic medical records associated with the patient and stored in electronic storage accessible by the first communication device, the first request including an authentication token stored on the electronic device is transmitted from the electronic device to a first communication device.

A second request for one or more electronic medical records associated with the patient and stored in electronic storage accessible by the second communication device is transmitted from the electronic device to a second communication device different than the first communication device, the second request including the authentication token stored on the electronic device.

At the electronic device from the first communication device, the one or more electronic medical records included in the first request is received, the one or more electronic medical records included in the first request being sent from the first communication device in response to the first communication device receiving the first request and authenticating the first request based on the authentication token.

At the electronic device from the second communication device, the one or more electronic medical records included in the second request is received, the one or more electronic medical records included in the second request being sent from the second communication device in response to the second communication device receiving the second request and authenticating the second request based on the authentication token.

Display is enabled of information related to the one or more electronic medical records received from the first communication device and the one or more electronic medical records received from the second communication device to a medical service provider providing a service to the patient.

Implementations may include one or more of the following features. For example, the electronic device associated with the patient may include a first electronic device and also include operations for establishing a secure connection between the first electronic device associated with the patient and a second electronic device associated with the medical service provider, the second electronic device being different than the first electronic device. The one or more electronic medical records received at the first electronic device from the first communication device and the one or more electronic medical records received at the first electronic device from the second communication device are transmitted from the first electronic device to the second electronic device over the secure connection.

The first communication device and the second communication device may be configured to deny requests, from the second electronic device, for electronic medical records associated with the patient because the second electronic device is unable to include the authentication token in requests for records.

One or more electronic medical records associated with the patient may be accessed from local storage associated with the electronic device. Enabling display, to the medical service provider providing a service to the patient, of information related to the one or more electronic medical records may include enabling display of the one or more electronic medical records accessed from local storage.

Filter criteria associated with the service being provided to the patient by the medical service provider may be accessed and transmitting, from the electronic device to the first communication device may include transmitting the filter criteria. Transmitting, from the electronic device to the second communication device different than the first communication device, a second request may include transmitting the filter criteria. Receiving, at the electronic device from the first communication device, the one or more electronic medical records may include receiving one or more electronic medical records that meet the filter criteria. Receiving, at the electronic device from the second communication device, the one or more electronic medical records may include receiving one or more electronic medical records that meet the filter criteria.

Enabling display, to the medical service provider providing the service to the patient, of information related to the one or more electronic medical records received from the first communication device and the one or more electronic medical records received from the second communication device may include rendering, on a display device associated with the electronic device, a display of the information related to the one or more electronic medical records received from the first communication device and the one or more electronic medical records received from the second communication device such that the medical service provider is able to perceive the electronic medical records.

The electronic device associated with the patient may include a first electronic device, and enabling display, to the medical service provider providing the service to the patient, of information related to the one or more electronic medical records received from the first communication device and the one or more electronic medical records received from the second communication device may include transmitting, from the first electronic device to a second electronic device associated with the medical service provider, the one or more electronic medical records received at the first electronic device from the first communication device and the one or more electronic medical records received at the first electronic device from the second communication device to enable display of the one or more electronic medical records received from the first communication device and the one or more electronic medical records received from the second communication device on a display device associated with the second device.

In another general sense, techniques and systems for accessing medical records are described. A process of aggregating electronic medical records associated with a patient is initiated, the process being initiated in response to the patient providing user input to an electronic device associated with the patient. In response to initiation of the process of aggregating electronic medical records associated with the patient, at least a first electronic medical records storage system and a second electronic medical records storage system that each store electronic medical records associated with the patient is identified, the second electronic medical records storage system being different from the first electronic medical records storage system.

First patient authentication information that enables retrieval of electronic medical records associated with the patient from the first electronic medical records storage system is identified. Second patient authentication information that enables retrieval of electronic medical records associated with the patient from the second electronic medical records storage system is identified. The second patient authentication information is different from the first patient authentication information.

A first request for medical records is generated using the first patient authentication information and a second request for medical records using the second patient authentication information is generated. The first request is transmitted from the electronic device to the first electronic medical records storage system.

The second request is transmitted from the electronic device to the second electronic medical records storage system. A first response including at least a first portion of one or more electronic medical records for the patient stored at the first electronic medical records storage system is received at the electronic device from the first electronic medical records storage system, the first response being sent from the first electronic medical records storage system in response to the first electronic medical records storage system receiving the first request and authenticating the first request based on the first patient authentication information.

A second response including at least a second portion of one or more electronic medical records for the patient stored at the second electronic medical records storage system is received at the electronic device from the second electronic medical records storage system, the second response being sent from the second electronic medical records storage system in response to the second electronic medical records storage system receiving the second request and authenticating the second request based on the second patient authentication information.

A set of electronic medical records associated with the patient is generated by combining the first portion of one or more electronic medical records for the patient included in the first response with the second portion of one or more electronic medical records for the patient included in the second response and display of the generated set of electronic medical records associated with the patient is enabled.

Implementations may include one or more of the following features. For example, receiving the first response may include receiving a first response that includes a first portion of a first electronic medical record for the patient stored at the first electronic medical records storage system and receiving the second response may include receiving a second response that includes a second portion of the first electronic medical record for the patient stored at the second electronic medical records storage system. Generating the set of electronic medical records may include combining the first portion of the first electronic medical record with the second portion of the first electronic medical record to generate a complete first electronic medical record.

The first and second responses may be configured to not include identifying information associated with the patient. Both the first request and the first response may be configured to not include information that identifies the second electronic medical records storage system such that interception of the first request and the first response does not lead to identification of electronic medical records stored in the second electronic medical records storage system. The first electronic medical records storage system and the second electronic medical records storage system may be configured to be unrelated and unaware of each other.

Identifying at least the first electronic medical records storage system and the second electronic medical records storage system, identifying first patient authentication information, identifying second patient authentication information, generating the first request, generating the second request, transmitting the first request, transmitting the second request, receiving the first response, receiving the second response, generating the set of electronic medical records, and enabling display of the generated set of electronic medical records may occur automatically, without human intervention, in response to initiation of the process of aggregating electronic medical records associated with the patient.

Identifying first patient authentication information may include identifying a machine token that enables retrieval of electronic medical records associated with the patient from the first electronic medical records storage system. Identifying second patient authentication information may include identifying a password that enables retrieval of electronic medical records associated with the patient from the second electronic medical records storage system, and generating the first request for medical records using the first patient authentication information may include generating a first request that includes the machine token. Generating the second request for medical records using the second patient authentication information may include generating a second request that includes the password.

Identifying first patient authentication information may include identifying a first patient identifier and a first password, the combination of the first patient identifier and the first password enabling retrieval of electronic medical records associated with the patient from the first electronic medical records storage system. Identifying second patient authentication information may include identifying a second patient identifier and a second password, the combination of the second patient identifier and the second password enabling retrieval of electronic medical records associated with the patient from the second electronic medical records storage system, the first patient identifier being different than the second patient identifier and the first password being different than the second password. Generating the first request for medical records using the first patient authentication information may include generating a first request that includes the first patient identifier and the first password. Generating the second request for medical records using the second patient authentication information may include generating a second request that includes the second patient identifier and the second password.

In yet another general sense, an emergency services provider is enabled to access medical records of a patient by receiving, at an electronic device of a patient and from an emergency services provider treating the patient, a request to access medical records associated with the patient. In response to receiving the request from the emergency services provider, based on authentication information provided to the electronic device by the emergency services provider, an authentication process is performed on the emergency services provider to determine a status of the emergency services provider;

Preferences of the patient regarding emergency services provider access to medical records of the patient is accessed from electronic storage. A level of access to the medical records associated with the patient is determined to provide to the emergency services provider based on the determined status of the emergency services provider and the accessed preferences of the patient.

Electronic medical records associated with the patient based on the determined level of access to provide to the emergency services provider are aggregated at the electronic device of the patient. Display, to the emergency services provider, is enabled of the aggregated electronic medical records associated with the patient.

Implementations may include one or more of the following features. Performing the authentication process on the emergency services provider to determine a status of the emergency services provider may include receiving input from a hardware device issued to the emergency services provider by an emergency services agency to enable authentication of the emergency services provider to the electronic device of the patient that is configured to aggregate electronic medical records associated with the patient, and determining a status of the emergency services provider based on the received input from the hardware device.

Performing the authentication process on the emergency services provider to determine a status of the emergency services provider may include receiving, from the emergency services provider, input indicating a user identifier and a password associated the emergency services provider, and determining a status of the emergency services provider based on the user identifier and the password.

Performing the authentication process on the emergency services provider to determine a status of the emergency services provider may include receiving, from the emergency services provider, input indicating a user identifier and a password associated the emergency services provider, receiving input from a hardware device issued to the emergency services provider by an emergency services agency to enable authentication of the emergency services provider to the electronic device of the patient that is configured to aggregate electronic medical records associated with the patient, and determining a status of the emergency services provider based on both the user identifier and the password and the received input from the hardware device.

Performing an authentication process on the emergency services provider to determine the status of the emergency services provider may include determining whether the emergency services provider is licensed and determining the level of access to the medical records associated with the patient to provide to the emergency services provider based on the determined status of the emergency services provider may include determining to provide access to at least some of the medical records associated with the patient in response to determining that the emergency services provider is licensed, and determining not to provide any access to the medical records associated with the patient in response to determining that the emergency services provider is not licensed.

Performing an authentication process on the emergency services provider to determine the status of the emergency services provider may include determining whether the emergency services provider is at least one of ambulance personnel, an emergency room doctor, and a surgeon that performs emergency surgery, and determining the level of access to the medical records associated with the patient to provide to the emergency services provider based on the determined status of the emergency services provider may include determining to provide a first level of access to the emergency services provider in response to determining that the emergency services provider is ambulance personnel, determining to provide a second level of access to the emergency services provider in response to determining that the emergency services provider is an emergency room doctor, the second level of access being different than the first level of access, and determining to provide a third level of access to the emergency services provider in response to determining that the emergency services provider is a surgeon that performs emergency surgery, the third level of access being different than the first level of access and the second level of access.

Determining the level of access to the medical records associated with the patient to provide to the emergency services provider based on the determined status of the emergency services provider and the accessed preferences of the patient may include determining the level of access from among at least three levels of access that include at least a full access level, a no access level, and an intermediate access level that is between the full access level and the no access level.

Aggregating, at the electronic device of the patient, electronic medical records associated with the patient based on the determined level of access to provide to the emergency services provider may include automatically aggregating electronic medical records without further input from the emergency services provider.

Performing the authentication process on the emergency services provider may include performing the authentication process without receiving input from the patient.

Performing the authentication process on the emergency services provider may include conditioning authentication of the emergency services provider on receiving a biometric input from the patient indicating that the patient is physically near the electronic device of the patient.

Implementations of the described techniques may include hardware, a method or process, or computer software on a computer-accessible medium.

The details of one or more implementations are set forth in the accompanying drawings and the description below. Other features will be apparent from the description and drawings, and from the claims.

DESCRIPTION OF DRAWINGS

Like reference symbols in the various drawings indicate like elements.

DETAILED DESCRIPTION

Figure 1A:
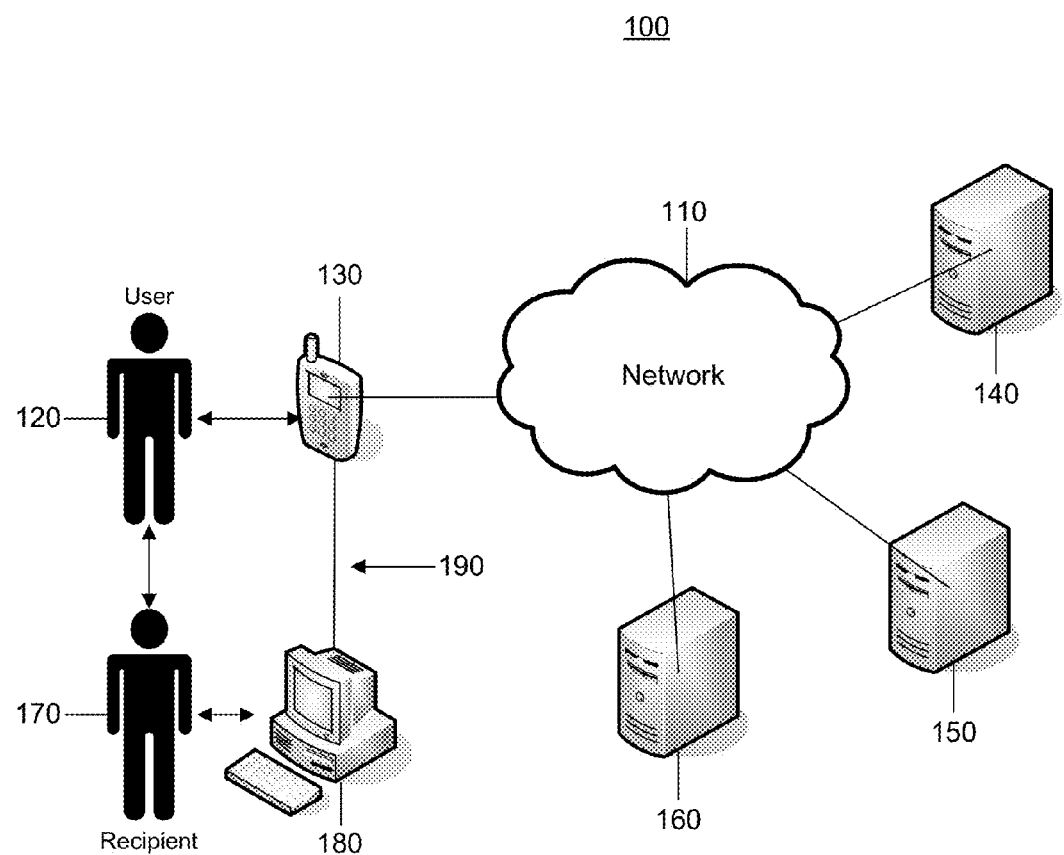
FIG. 1A is a block diagram of an example system configured to perform records access and management.

In some implementations, a mobile device associated with a user is configured to securely aggregate electronic medical records for the user. The mobile device may be configured to serve as a real-time, secure conduit to receive electronic medical records from remote service providers such that the electronic medical records may be displayed to a medical service provider that/who provides medical service to the user. For example, if a user attends a doctor's appointment and the doctor does not have necessary medical record's for the user, the user may use the user's mobile device to quickly access the electronic medical records needed by the doctor. In another example, if a user is involved in a car accident and an emergency services provider is providing treatment to the user, the user's mobile device may be used to access electronic medical records for the user that may assist the emergency services provider in providing emergency treatment to the user. In these examples, treatment or diagnosis of the user may be improved because the medical service provider is able to make a complete review of the relevant medical records and is able to access the relevant medical records in a timely manner.

For example, in one implementation, a user of a mobile device may initiate a request to aggregate medical records associated with the user. The mobile device responsively sends requests to multiple different database providers (e.g., a hospital database, a medical records database provider, a pharmacy database, etc.) that store electronic medical records for the user. The multiple database providers send the requested medical records for the user to the mobile device, enabling the mobile device to render a display of information related to the received medical records. The user may then present the display to a medical service provider (e.g., a doctor) providing care to the user for review of the medical records. The mobile device may be configured to transfer the received medical records to an electronic device of the medical service provider, such that the mobile device acts as a secured conduit for medical records. In this manner, through the use of security on the mobile device, access to the medical records may be securely accessed through the use of the mobile device as a conduit. Moreover, the mobile device may be configured to request only a subset of the medical records of the user related to treatment that the doctor is providing. Because the subsets of medical records are distributed across multiple storages, a single point of failure (e.g., security breach) at a particular fragmented storage may not compromise the entire record. Each fragment also may be known as a stub, or a segment, or a portion. Further, data segments deemed more sensitive (or stigmatic) may be stored with a higher level of security. To implement security, each data segment may be encrypted with varying levels of sophistication. Additionally, the mobile device may be configured to enable the user and/or the medical service provider to add a medical record for the user.

In some implementations, an electronic device may serve as a distributable, remotely accessible and secure electronic medical record proxy, where the contemplated proxy aggregates from storage, separately-stored pieces of a user's medical record using an identifier that is tied to their disaggregated identity. Portions of records then may be separately stored in multiple locations. To deter alternation/tampering, integrity checking mechanisms may be implemented for each portion to enforce non-repudiation. In particular, each portion may be stored at separate network locations with a respective error checking code. For example, each portion may include a hash code generated from the payload data of the portion. For illustration, a MD5 hash may be generated for each portion to deter alteration therein. Watermarks also may be generated for each portion for the same purpose. Each portion may not contain information identifying the user who owns the data. Each portion may include a unique identifier that does not identify the user but can link the stored portions together. The recipient party that views/accesses the proxy perceives a single file. However, the perceived file is a virtual assemblage of a stored user identity with more than one stored component of a complete medical record, using a common key. This allows aggregation of data from all over the world. That is, the recipient gets a simple looking file. Yet the recipient (e.g., the user/patient) gets to control what the file includes, and only the recipient knows the sources from which it is assembled. Moreover, the recipient may be assured of privacy because the recipient's name (or other identifying information) is disaggregated from the file, and even in the event of a breach, the segmentation of the de-identified medical record may render the compromised data segment useless to the intruder (or a person who has inadvertently obtained the data segment).

Notably, a chain of trust may be established. For instance, an electronic medical record may have a digital certificate attached. The digital certificate may include a public key of the submitting party, as issued by a certificate authority, also known as CA. In this instance, the electronic medical record may be encrypted by a private key of the submitting party such that the encrypted electronic medical record can only be decrypted by the public key of the submitting party. Such asymmetric encryption/decryption may cause the contents of the electronic medical record to remain authentic. The asymmetric encryption/decryption also may deter tampering or alteration by other parties. In another example, the electronic medical record may include a digital watermark uniquely identifying the submitting party. In this particular example, the digital certificate may include, for example, a digital signature of the submitting party. The correlation between the digital signature in the digital certificate and the digital signature as embedded in the electronic medical record may prevent alteration and tampering of the electronic medical record by other parties during distributed storage of the electronic medical record.

In some examples, emergency service providers (e.g., 911 service providers, emergency medical technicians, etc.) may be provided with a key to the medical records, which is accessed based on a code that is on the person associated with a medical record (e.g., wrist or key chain) being read by a third party who themselves may be identified as emergency personnel. The code also may be supplied by an emergency services operator or other service provider that manages emergency access to the recipient's medical records. Two factor identification may be used to enable emergency access in this context (e.g., the emergency service provider may need to enter a code and possess a particular device or hardware key only available to licensed emergency service providers to access medical records). Moreover, the code of the person associated with a medical record may be hidden (e.g., a secure ID and a bracelet code may be required for attempted access).

A medical power of attorney may allow a principal to designate healthcare decisions to an appointed agent in the event that the principal is rendered unable to make the decision. A caregiver for a senior citizen may have medical power of attorney over the senior citizen. The caregiver may access medical records of the senior citizen without having to go through the senior citizen. In particular, the caregiver may request information as necessary for rendering care for the senior. The caregiver may not access information irrelevant for the caregiver to render the medical care. Moreover, the caregiver may interact with social media channels on behalf of the senior. The caregiver may even report medical information of the senior during medical studies—for example, a clinical trial for a drug for treating the Alzheimer's disease—involving the senior citizen. Likewise, a child custodian may have similar medical power of attorney over the child and may similar access privileges to the medical records of the child. In these situations, a chain of trust may be established in accordance with the disclosure herein.

A user-configurable online profile may be used to limit information that is provided to an emergency services provider. The online profile may be used to regulate the information based on the status of the emergency personnel (e.g., ambulance driver gets low level; trauma gets higher level, etc.). Specifically, a user may choose to release medication to regular doctors, and release more access (e.g., full access) to trauma providers. The system also may be configured to release all information to the multiple parties of different level at the same time (e.g., provide an ambulance driver with limited information, and concurrently provide local emergency room personnel with deeper access to provide them time to prepare for the inbound patient).

Moreover, the user may configure a persistence parameter for the user's medical record data gathered from various storage locations. Depending on the context, the user may desire different durations for the aggregated medical care record. The aggregated medical record information may be available on the display of the user's mobile device for a limited period of time, in situations where the healthcare professionals may only need to view the information temporarily, for example, for confirmation purposes only. In these situations, the rendered display information may not be printed to a printer or beamed to a device at the doctor's office. In situations where the aggregated medical care record is transmitted to the device at the doctor's office, the aggregated medical record data may expire after the limited period of time, for example, with the expiration of a password used to encrypt the aggregated medical record. In other situations, the user may desire a longer duration, including permanent storage, when the user expects to revisit the same doctor's office for follow-up visits.

Referring to FIG. 1A, a system 100 is configured to perform records access and management. The system 100 includes a user 120, a user electronic device 130, multiple record storage systems 140, 150, and 160, a recipient 170, and a recipient electronic device 180. The user electronic device 130 may be configured to exchange electronic communications with the multiple record storage systems 140, 150, and 160 over network 110. The user electronic device 130 may also be configured to exchange electronic communications with the recipient electronic device 180 over connection 190.

The network 110 is configured to enable exchange of electronic communications between devices connected to the network 110. For example, the network 110 may be configured to enable exchange of electronic communications between the user electronic device 130 and the multiple record storage systems 140, 150, and 160. The network 110 may include, for example, one or more of the Internet, Wide Area Networks (WANs), Local Area Networks (LANs), analog or digital wired and wireless telephone networks (e.g., a PSTN, Integrated Services Digital Network (ISDN), a cellular network, and Digital Subscriber Line (xDSL)), radio, television, cable, satellite, and/or any other delivery or tunneling mechanism for carrying data. Network 110 may include multiple networks or subnetworks, each of which may include, for example, a wired or wireless data pathway. The network 110 may include a circuit-switched network, a packet-switched data network, or any other network able to carry electronic communications. For example, the network 110 may include networks based on the Internet protocol (IP) or asynchronous transfer mode (ATM).

The user 120 is a person that operates a user electronic device. For example, the user 120 may provide user input to the user electronic device 130 to perform operations on the user electronic device 130. In some implementations, the user 120 is a patient receiving medical treatment from a doctor. In these implementations, the patient may operate the user electronic device 130 to retrieve electronic medical records of the user 120 to assist in treatment at the time of treatment or prior to treatment.

The user electronic device 130 is an electronic device configured to communicate over a network to perform electronic records access and management operations. The user electronic device 130 may be any type of electronic device configured to exchange communications over the network 110 to request electronic records and receive electronic records. For example, the user electronic device 130 may be a personal computer, a server, or a mobile device. For example, the user electronic device 130 may be a wireless phone, a cellular phone, a mobile personal digital assistant (PDA) with embedded cellular phone technology, or a smart phone. The user electronic device 130 may include an integrated display configured to display record information and/or may be configured to control a separate display to display record information. The user electronic device 130 may include multiple electronic components and may include multiple electronic devices. In some implementations, the user electronic device 130 may be configured to access electronic medical or health records for the user 120 and render a display of the medical or health records on a display associated with the user electronic device 130. In these implementations, the user 120 may show the display to the medical service provider to enable the service provider to perceive the electronic medical records. In other implementations, the user electronic device 130 may be configured to establish a connection with a device associated with the medical service provider and transmit the electronic medical records to the device to enable the medical service provider to display and/or store the electronic medical records.

The multiple record storage systems 140, 150, and 160 are electronic systems configured to store electronic data and exchange communications over a network. The multiple record storage systems 140, 150, and 160 may be electronic systems configured to store electronic records and exchange communications with the user electronic device 130 over the network 110. For example, the multiple record storage systems 140, 150, and 160 may include a personal computer, a server, or a database. Each of the multiple record storage systems 140, 150, and 160 includes a storage or memory device configured to store electronic data. The storage or memory device may be configured to store date using, for example, magnetic, optical, and/or solid state technologies. For example, the storage or memory device may include a hard disk, a tape drive, a compact diskette, a random access memory ("RAM"), and/or a read-only memory ("ROM"). The multiple record storage systems 140, 150, and 160 may include multiple electronic components and/or multiple electronic devices or systems. Although three record storage systems are shown in FIG. 1, any number of record storage systems may be connected to the network 110. In some implementations, the multiple record storage systems 140, 150, and 160 store electronic medical records associated with the user 120 and are configured to send the electronic medical records to the user electronic device 130 upon request. In these implementations, the multiple record storage systems 140, 150, and 160 may be associated with one or more of a doctor, a hospital, a pharmacy, an insurance company, a records storage company, another type of medical service provider, or another type of organization that stores electronic medical records.

The recipient 170 is a person that operates a recipient electronic device. For example, the recipient 170 may provide user input to the recipient electronic device 180 to perform operations on the recipient electronic device 180. In some implementations, the recipient 170 may be a medical service provider (e.g., a doctor) providing treatment to the user 120 and may use the recipient electronic device 180 to access electronic medical records for the user 120 to assist in treating the user 120. The medial service provider may be known as a healthcare professional, or a healthcare provider.

The recipient electronic device 180 is an electronic device configured to communicate with other electronic devices to perform records access and management operations. The recipient electronic device 180 may be any type of electronic device configured to exchange communications over the connection 190. For example, the recipient electronic device 180 may be a personal computer, a server, or a mobile device. For example, the recipient electronic device 180 may be a wireless phone, a cellular phone, a mobile personal digital assistant (PDA) with embedded cellular phone technology, or a smart phone. The recipient electronic device 180 may include an integrated display configured to display record information and/or may be configured to control a separate display to display record information. The recipient electronic device 180 may include multiple electronic components and may include multiple electronic devices. In some implementations, the recipient electronic device 180 may be configured to receive medical records for the user 120 from the user electronic device 130 and render a display of the electronic medical records on a display associated with the recipient electronic device 180. The recipient electronic device 180 may be a computer system operated by a medical service provider (e.g., a doctor) in a treatment facility (e.g., a doctor's office or a hospital).

The connection 190 is configured to enable exchange of electronic communications between devices connected to the connection 190. For example, the connection 190 may be configured to enable exchange of electronic communications between the user electronic device 130 and the recipient electronic device 180. The connection 190 may include a wired or wireless data pathway. For example, the connection 190 may be a Bluetooth connection between the user electronic device 130 and the recipient electronic device 180. In one configuration, the connection may include a radio-frequency (RF) link for user electronic device 130 and recipient electronic device 180 to beam data to each other. In another configuration, the connection may include an infra-red (IR) link for user electronic device 130 and recipient electronic device 180 to exchange data. In another example, the connection 190 is a direct wired connection between only the user electronic device 130 and the recipient electronic device 180 (e.g., a universal serial bus (USB) connection, an IEEE 1394 (Fire Wire) connection, etc.). In this example, the direct wired connection ensures a secure transfer between the user electronic device 130 and the recipient electronic device 180 because other devices cannot intercept communications over the direct wired connection. In yet another example, the connection may include a scanning mechanism through which recipient electronic device 180 may scan a symbology on the display of user electronic device 130. The symbology may include bar codes, QR codes, or even textual information. The scanning mechanism may include a scanner with a light source and a light sensor. The light source may include, for example, photodiodes such as LEDs for efficient operation. The light source may operate in visible or infra-red (IR) spectra. The light source may cause the symbology to be illuminated. In some implementations, the illumination may be modulated to provide security. The light sensor may then receive optical signals caused by the illuminated symbology. The light sensor may include, for example, an IR sensor, a charge-coupled device (CCD), or an optical camera. In some implementations, the connection 190 is a network similar to the network 110. In other implementations, the connection 190 is not necessary and the user electronic device 130 and the recipient electronic device 180 may exchange electronic communications over the network 110. In some implementations, the connection 190 facilitates a secure exchange of electronic medical records to maintain integrity and privacy of electronic medical records exchanged over the connection 190. For example, the connection 190 may be a direct wired connection between only the user electronic device 130 and the recipient electronic device 180 as described above. In other examples, the connection 190 facilitates a virtual private network (VPN) connection or another type of authenticated and/or encrypted connection sufficient to reasonably secure data exchanged over the connection 190.

Figure 1B:
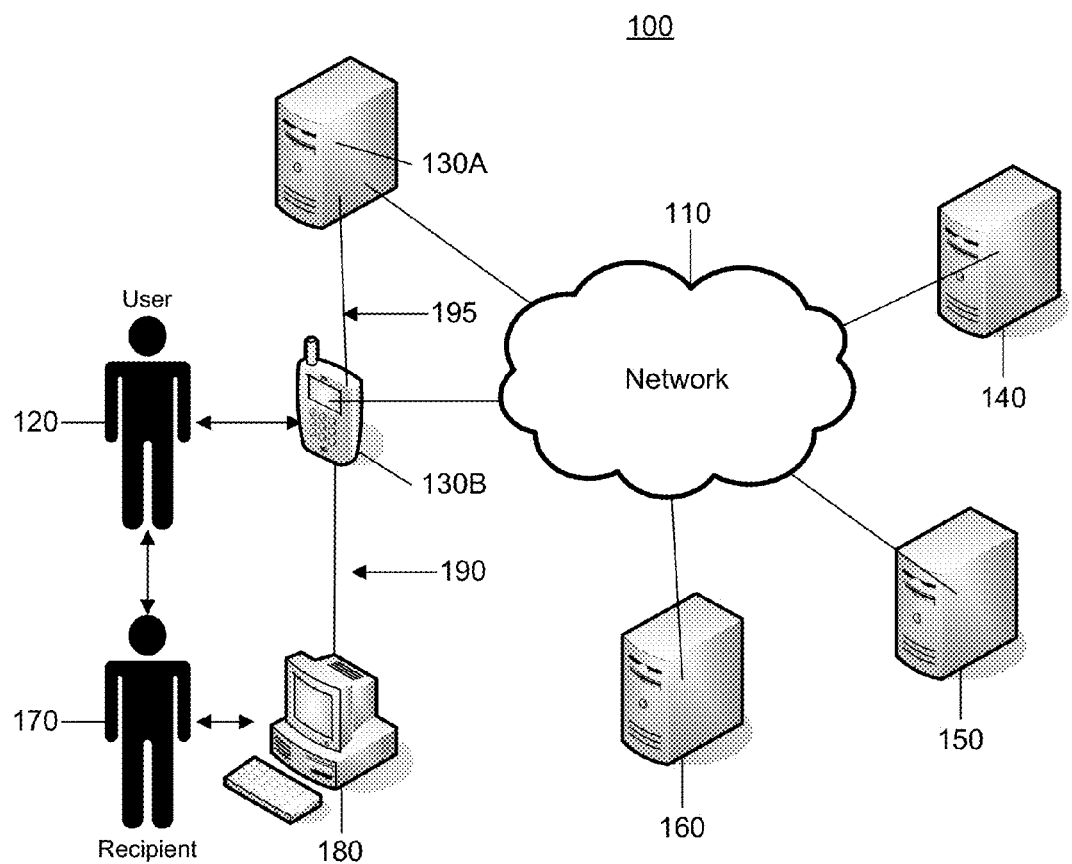
FIG. 1B is a block diagram of another example system configured to perform records access and management.

FIG. 1B shows another example system 100 configured to perform records access and management. In particular, the electronic device 130 may function as a user device as well as a server for a patient to process electronic medical records therefrom. As disclosed herein, some implementations may include multiple instances of electronic device 130 to process electronic medical records as well as to interact with electronic medical records storage systems 140, 150, and 160. In one instance, the electronic device 130 may include an electronic device 130B carried by a patient as well as an ancillary data server 130A on which a service provider may store, for example, addresses of electronic medical records of the patient. In this context, the service provider may provide a service to access the distributed electronic medical record, for example, on-demand. The ancillary data server 130A may thus function as, for example, a back-up server to the electronic device 130B by keeping a copy of the address information. The copy of address information may be synchronized with the copy on electronic device 130B regularly. The synchronization may also occur on each update of the copy on electronic device 130B. In case the electronic device 130B loses the copy thereon, for example, due to storage malfunction or operator error, the backup copy on ancillary data server 130A may be relied on by electronic device 130B. Communication between electronic device 130B and ancillary data server 130A may be carried out over connection 195. Similar to connection 190, connection 195 facilitates a secure exchange of electronic medical records to maintain integrity and privacy of electronic medical records exchanged over the connection 195. For example, connection 195 may include a virtual private network (VPN) connection or another type of authenticated and/or encrypted connection sufficient to reasonably secure data exchanged over the connection 195. In another exemplary embodiment, ancillary data server 130A could be another electronic device owned and operated by the User, such as a PC, network attached storage (NAS), or another electronic device.

Figure 2:
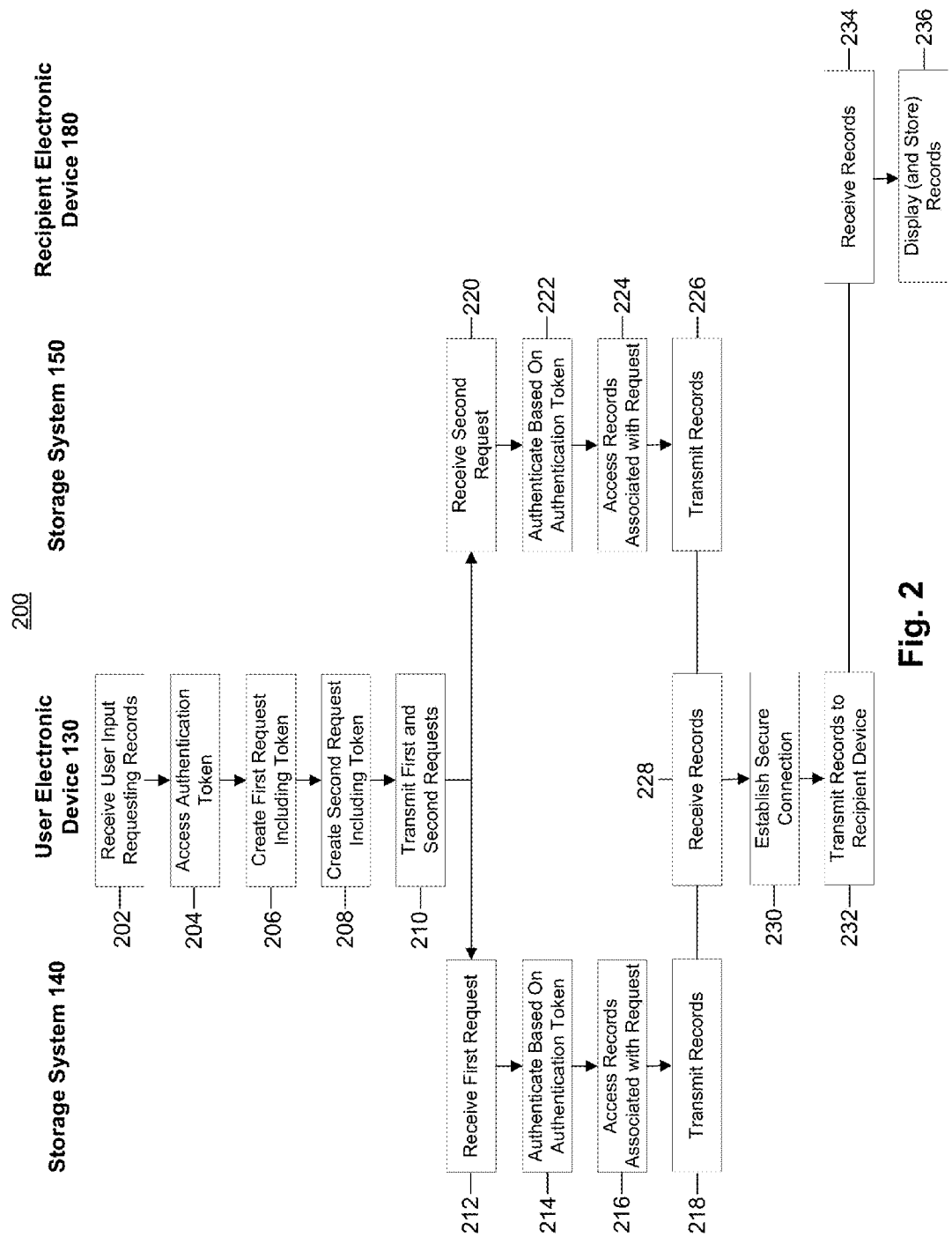
FIG. 2 is a flow chart of a process for accessing and presenting records.

FIG. 2 is a flow chart of a process 200 for accessing and presenting electronic medical records. For convenience, particular components described with respect to FIG. 1 are referenced as performing the process 200. However, similar methodologies may be applied in other implementations where different components are used to define the structure of the system, or where the functionality is distributed differently among the components shown by FIG. 1.

The user electronic device 130 receives user input requesting records (202). In some implementations, the user electronic device 130 may receive user input provided by the user 120 indicating a request for electronic medical records associated with the user 120. For example, the user 120 may provide user input to the user electronic device 130 indicating a request for electronic medical records by selecting an icon that is rendered on a graphical user interface of a display associated with the user electronic device 130 and that is configured to initiate a request for electronic medical records. In another example, the user 120 may enter, using a keyboard or keypad, a command into a user interface rendered on a display associated with the user electronic device 130 to request electronic medical records. In some implementations, a user 120 may submit a request for electronic medical records by interacting with a user interface rendered on a display associated with the user electronic device 130 (e.g., the interface 400 described below with respect to FIG. 4). In other implementations, a medical service provider may operate the user electronic device 130 to initiate a request for electronic medical records associated with the user 120. In these implementations, storage systems storing electronic medical records for the user 120 may require input (e.g., authentication credentials) from the medical service provider to authenticate or authorize the request for electronic medical records prior to sending the electronic medical records to the user electronic device 130.

The user electronic device 130 accesses an authentication token (204). For example, the user electronic device 130 accesses a hardware specific machine token stored in electronic storage associated with the electronic user device 130. In this example, the hardware specific machine token may be configured to enable a storage system (e.g., storage systems 140 and 150) to identify and authenticate the electronic device making a request for electronic medical records. The hardware specific machine token may be specific to the user electronic device 130 such that a storage system (e.g., storage systems 140 and 150) may verify that a request for electronic records for a particular patient has been received from a physical device associated with the patient. In this example, requests for electronic medical records associated with the user 120 may be denied unless received from the user electronic device 130 associated with the user 120. For example, the user 120 may be receiving treatment from a doctor at the doctor's office. The doctor may ask the user 120 a question about the user's medical history to which the user does not know the answer. In response, the user 120 may use the user electronic device 130 as a secure conduit to access electronic medical records for the user to answer the question posed by the doctor. By enabling the user 120 to quickly access his or her electronic medical records, the user 120 may be able to provide the doctor with accurate information needed for treatment in real time or at least without the delays associated with requesting medical records and having the medical records delivered to the doctor's office. Moreover, in this example, because the request must be from the user electronic device 130, reasonable security measures are provided to ensure privacy of electronic medical records for the user 120.

In other implementations, the authentication token may include or enable determination of other types of authentication information such as authentication credentials (e.g., a user name and password), cookies, encrypted keys, or other types of authentication information. In some examples, a patient (or medical service provider) may be required to enter authentication credentials and the authentication credentials may be used as part of the authentication token. In these examples, the authentication credentials may be combined with a hardware specific machine token such that requests for electronic medical records associated with the user 120 may be denied unless the requests are received from the physical user electronic device 130 associated with the user 120 and include valid authentication credentials of the user 120 and/or a medical service provider.

To enable a medical service professional to access electronic medical records received at user electronic device 130, the medical service professional may be authenticated. The authentication may be based on a combination of hardware and software tokens of the medical service professional. The authentication may be performed at the user's electronic device 130. The authentication may also be performed at a remote server of an identity providing party (IdP) with the user as the relying party. The authentication may ensure the legitimacy of the data access. In some implementations, a valid hardware specific machine token and authentication credentials from an approved or certified medical service provider (other than the patient) may be sufficient to authenticate a request for electronic medical records associated with the patient. For example, a storage system storing electronic medical records may include a list of approved or certified medical service providers and authentication credentials associated with the medical service providers. In this example, a medical service provider may submit a request for electronic medical records for the user 120 using the user electronic device 130. The medical service provider may provide authentication credentials with the request and the storage system storing electronic medical records for the user 120 may authenticate the medical service provider. In response to authenticating that the request is from an approved medical service provider and from the user electronic device 130 associated with the user 120, the storage system may provide the requested electronic medical records for the user 120 to the user electronic device 130 for display on the user electronic device 130. In this example, the user may configure the list of approved or certified medical service providers, as stored at the particular storage system. The user may further issue a credential token to each of the approved or certified medical service providers, as an illustration, using a private key of the user. The credential token may be issued to a particular approved or certified medical service provider encrypted using a public key of the particular approved or certified medical service provider so that only the particular approved or certified medical service provider may decrypt the encrypted credential. The issued credential may be revoked by the user during a re-configuration of the list of approved or certified medical service providers. In this example, an approved medical service provider providing emergency care to the user 120 may be able to quickly access electronic medical records for the user 120 in a situation in which the user is incapacitated or otherwise unable to request electronic medical records and the medical service provider has access to the user electronic device 130. For example, the user 120 may be a victim of an accident in which the user 120 has a head injury and is unconscious. In this example, a medical service provider at the scene providing emergency care to the user 120 may obtain the user electronic device 130 from the person of the user 120, enter authentication credentials, and access electronic medical records for the user 120. By enabling the medical service provider to access the electronic medical records for the user 120, the medical service provider may be able to provide more effective and safer treatment to the user 120. Moreover, in this example, because the request must be from an approved medical service provider and from the user electronic device 130, reasonable security measures may be provided to ensure privacy of electronic medical records for the user 120.

The user electronic device 130 creates a first request for electronic medical records based on the accessed authentication token (206). For example, the user electronic device accesses information associated with a first storage system (e.g., storage system 140) storing electronic medical records included in the request and generates a request for the electronic medical records stored by the first storage system based on the accessed information and the accessed authentication token. In some examples, the accessed information may include information related to a network address for the first storage system and formatting information for requests to the first storage system. In these examples, the user electronic device 130 may generate a request addressed to the first storage system and in a format used by the first storage system. The user electronic device 130 also includes information associated with the accessed authentication token in the first request. For example, the user electronic device 130 may include the authentication token in the first request or otherwise generate the request to include information based on the accessed authentication token. For example, the user electronic device 130 may encrypt the first request using information included in the authentication token such that the storage system only will be able to decrypt the request if the request was encrypted with a valid authentication token. The first request also may include information identifying the user and/or the electronic medical records asked for in the request. However, the requested information segment for the electronic medical record may not include information identifying the user. As disclosed herein, a particular electronic medical record may be segmented and each segment stored at separate storage. To mitigate the risks of data breach, each segment is not only stripped of information identifying the patient (the user) but also encrypted by a key unique to the patient (for example, the public key of the user). To counter data alteration/tampering, the segment also may include integrity check. In one example, a hash code (e.g., a MD5 hash) may be generated for the segment and embedded with the data segment in a manner unknown to an intruder. The embedding location could be secretive and only known to the user. In another example, the hash code could be stored elsewhere and data integrity may be confirmed only upon a successful comparison. The hash code example is only one illustration. Other integrity check codes may be applied as well. For example, a cyclic redundancy code, or an error checking code.

The user electronic device 130 creates a second request for electronic medical records based on the accessed authentication token (208). The user electronic device 130 may create the second request in a manner similar to creating the first request described above with respect to step 206. The second request may be addressed a second storage system (e.g., storage system 150) storing electronic medical records included in the request. The second storage system may be different from the first storage system. Accordingly, the second request may include a different address and may be in a different format than the first request.

The user electronic device 130 transmits the first request to the storage system 140 and the second request to the storage system 150 (210). For example, the user electronic device 130 may transmit the first request for electronic medical records to the storage system 140 as an electronic communication over the network 110, and the user electronic device 130 may transmit the second request for electronic medical records to the storage system 150 as an electronic communication over the network 110. The user electronic device 130 may transmit the first request and second request at the same time or may transmit the first request before or after the second request. For example, the user electronic device 130 may transmit the first request to the storage system 140 and wait to receive a response from the storage system 140 prior to transmitting the second request. In this example, the user electronic device 130 may analyze the response from the storage system 140, customize or modify the second request to only request electronic medical records not received in the response from the storage system 140, and transmit the modified second request to the storage system 150.

The storage system 140 receives the first request (212). For example, the storage system 140 receives, from the user electronic device 130, the first request for electronic medical records over the network 110. The first request may include information sufficient for the storage system 140 to identify a user, identify the requested electronic records for the user, and the authentication token.

The storage system 140 authenticates the first request based on the authentication token (214). For example, in implementations in which the authentication token includes a hardware specific machine token, the storage system 140 extracts the hardware specific machine token from the first request and authenticates the first request based on the hardware specific machine token. In this example, the storage system 140 may compare the hardware specific machine token with a known token associated with the user 120 associated with the first request and authenticate the first request based on the comparison. Because the hardware specific machine token is specific to the user electronic device 130, the storage system 140 may be configured to only authenticate requests received from the user electronic device 130.

In some implementations, the authentication token may include authentication credentials for the user 120 associated with the request for records or a medical service provider. In these implementations, the storage system 140 may extract the authentication credentials from the authentication token, compare the authentication credentials with known authentication credentials for the user 120 or the medical service provider, and authenticate the first request based on the comparison. Because the authentication credentials are specific to the user associated with the records or an approved medical service provider, the storage system 140 may be configured to authenticate requests based on the person making the request. Authenticating the first request based on authentication credentials may be performed in addition to, or in lieu of, authenticating the first request based on a hardware specific machine token.

The storage system 140 accesses electronic medical records associated with the first request (216). For example, the storage system 140 may access, from electronic storage associated with the storage system 140, electronic medical records associated with the first request. In this example, the storage system may access all electronic medical records associated with a user identified in the first request or may access specific electronic records identified by the first request. In some implementations, the first request may include restrictions or conditions on the electronic medical records requested in the first request. For example, the first request may indicate that only certain types of electronic medical records (e.g., only orthopedic medical records) or only electronic medical records from a certain time period (e.g., only electronic medical records from within the last five years) should be accessed. In this example, the storage system 140 may access the electronic medical records for the user based on the restrictions or conditions. In other examples, restrictions or conditions may be associated with particular users or may be set by a user in advance. For example, an orthopedic doctor only may be able to access records associated with orthopedic treatment and prevented from accessing other types of medical records that may be irrelevant to orthopedic treatment, such as, for example, hair loss or skin rash. In another example, a user may set restrictions or conditions on record requests with the storage system 140 in advance and the storage system 140 may be configured to handle record requests based on the restrictions or conditions set by the user. In this example, a user may decide to prevent particularly embarrassing or distressing medical records from being accessed via a record request and the storage system 140 may prevent access to those records when electronic requests for records are received. For example, information on particular conditions (e.g., herpes, HIV, erectile dysfunction, unexpected pregnancy, miscarriage) may require special access authorization. The storage system 140 may be configured to provide a message to a person requesting the restricted records that access to the records has been restricted by the user.

The storage system 140 transmits the accessed electronic medical records to the user electronic device (218). For example, the storage system 140 may transmit the accessed electronic medical records to the user electronic device 130 as one or more electronic communications over the network 110. Transmission of the electronic medical records may be a secure transmission of electronic medical records. For example, the electronic records may be encrypted and may be transmitted using another type of secure technology for transmitting electronic information over a network. In addition, transmission of the electronic records may include transmitting authentication information (e.g., an authentication token as described with respect to the user electronic device 130). The authentication information may be employed by the user electronic device 130 to authenticate the electronic medical records so that the user electronic device 130 may verify that the electronic medical records are legitimate.

The storage system 150 receives the second request (220), authenticates the second request (222), accesses electronic medical records associated with the second request (224), and transmits the accessed electronic medical records to the user electronic device (226). The storage system 150 may perform steps 220-226 using techniques similar to those described above with respect to the storage system 140 performing steps 212-218. Although requests for electronic medical records are shown as being sent to two storage systems, requests for electronic medical records may be sent to more than two storage systems or only a single storage system. The mechanism as disclosed herein may rely on a distributed storage model in which a particular electronic medical record may be divided into segments with each segment stored at different storage over network 110. The distribution may substantially reduce the chance of data breach caused by a single point of failure. Further, each segment may be stored with encryption or integrity checking features as disclosed herein.

Notably, a chain of trust may be established for a particular electronic medical record. The chain of trust may include an authenticity feature of the particular electronic medical record, that is, the particular electronic medical record is authentic as submitted by the purported submitting party. This authenticity feature includes the capability to prove the particular electronic medical record has not been altered or tampered with since the particular electronic medical record was submitted. The chain of trust may also include a non-repudiation feature of the particular electronic medical record. In other words, the electronic medical record has specific features that prevent the authenticity from being repudiated.

In some instances, a certificate authority (CA) may provide the digital certificates as well as a public/private key infrastructures (PKI) for participating entities, including, for example, the individual patients, healthcare professionals, or health insurance carriers. For instance, hospitals (or healthcare professionals) may submit electronic medical records with a proof of authenticity (such as, for example, a digital certificate). In these instances, the electronic medical records may be encrypted with a private key of the submitting party and the corresponding public key may be attached to the encrypted medical records. The public key may include digital signature of the CA as prima facie proof of legitimacy. Using the PKI, the authenticity of the underlying electronic medical records may be verified. In these instances, the submitting party may be a healthcare provider, such as a hospital, treating physician, or attending nurse. The submitting party may also include a health insurance carrier, such as an insurance payor. In one instance, the submitting party may also include the individual patient whose medical record is being submitted electronically.

In some instances, from the perspective of a patient, the authentication mechanism also may include a biometric mechanism linking the data record to the patient. The biometric information may function as an encryption key in a symmetric encryption/decryption mechanism to encrypt medical record data. The biometric information may include digitized finger print, iris-scan, retina-scan, etc. The biometric mechanism may allow electronic medical records to be decrypted at the user's electronic device 130 based on the biometric information of the user (e.g., a finger print).

The proof of authenticity may attest to the validity of the electronic medical record, much like an electronic postmark to indicate, for example, originating hospital and destination storage.

In some instances, the electronic postmark may further include integrity check codes to attest to the integrity of the underlying electronic medical record. The integrity check codes may generally include checksums, hash codes, error checking codes. The integrity check codes also may be encrypted by a private key of the PSO to counter forgery or tampering thereof. In other words, the integrity check mechanism may enforce a non-repudiation feature of a particular electronic medical record to prevent any alteration or tampering thereof.

The user electronic device 130 receives the electronic medical records from the storage system 140 and the storage system 150 (228). For example, the user electronic device 130 receives the electronic medical records from the storage system 140 and the storage system 150 in electronic communications sent over the network 110. In this example, the electronic communications and electronic medical records may be encrypted, exchanged over a secure connection, or otherwise protected against unwanted or improper access. The electronic communications and electronic medical records may include authentication information with which the user electronic device may authenticate the received electronic medical records to ensure that the received electronic medical records are authentic. In some implementations, the user electronic device 130 may be configured to render a display of the received electronic medical records. In these implementations, a medical service provider may view the electronic medical records on the display rendered by the user electronic device 130 when providing treatment or services to the user.

The user electronic device 130 establishes a secure connection with the recipient electronic device 180. For example, the user electronic device 130 may establish a secure connection with the recipient electronic device 180 over connection 190. In some examples, the user electronic device may be configured to establish a secure connection with the recipient electronic device 180 over a wired connection between only the user electronic device 130 and the recipient electronic device 180 (and perhaps other trusted devices). For instance, in these examples, the user electronic device 130 may establish a wired connection with a computer in a doctor's office over a direct USB connection or may establish a wired connection with the computer in the doctor's office over a local area network included in the doctor's office. In other examples, the user electronic device 130 may establish a secure connection with the recipient electronic device 180 over a wireless connection.

The user electronic device 130 transmits the electronic medical records over the secure connection to the recipient electronic device (232) and the recipient electronic device receives the electronic medical records (234). For example, the user electronic device 130 may transmit the electronic medical records to the recipient electronic device 180 in electronic communications over the secure connection and the recipient electronic device 180 may receive the electronic communications.

The recipient electronic device 180 displays and, optionally, stores the electronic medical records (236). For example, the recipient electronic device 180 may render a display of the received electronic medical records on a display device associated with the recipient electronic device 180 such that a medical service provider may view the electronic medical records on the display rendered by the recipient electronic device 180 when providing treatment or services to the user. In this example, the recipient electronic device 180 may display an x-ray image or an electronic medical chart entry received with the electronic medical records. The recipient electronic device 180 also may store, in electronic storage, the electronic medical records for record purposes and later retrieval.

Figure 3:
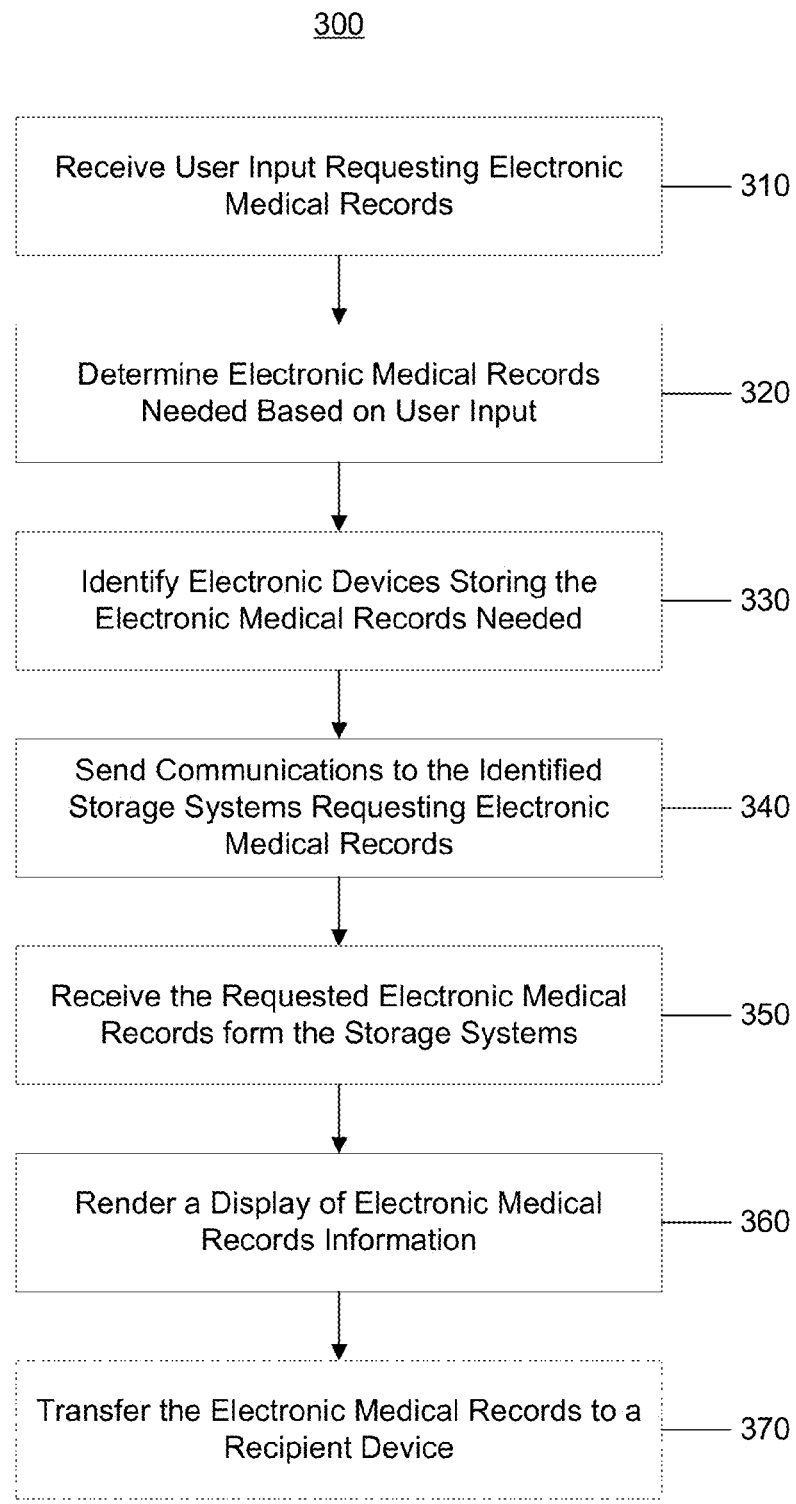
FIG. 3 is a flow chart of a process for accessing and presenting records.

FIG. 3 is a flow chart of a process 300 for accessing and presenting electronic medical records. For convenience, particular components described with respect to FIG. 1 are referenced as performing the process 300. However, similar methodologies may be applied in other implementations where different components are used to define the structure of the system, or where the functionality is distributed differently among the components shown by FIG. 1.

The user electronic device 130 receives user input requesting electronic medical records (310). For example, the user 120 may supply user input (e.g., using a keyboard, keypad, mouse, stylus, etc.) to the user electronic device 130 to initiate a request for electronic medical records. In other examples, the recipient 170 may enter user input to the user electronic device 130 or the user electronic device 130 may receive user input over connection 190 or network 110 from, for example, the recipient electronic device 180. For context, the disclosure herein generally may not rely on a caching mechanism to retain a local copy of the electronic medical records on user electronic device 130 or recipient electronic device 180. Specifically, user electronic device 130 may not store electronic medical records for future use. Likewise, healthcare professionals may not wish to retain copies of electronic medical records longer than necessary on recipient electronic device 180, the breach of which may give rise to unwarranted risks to the patients. Electronic medical records may include sensitive information, the breach of which may be highly undesirable.

The user electronic device 130 determines the electronic medical records needed based on the user input (320). For example, the user electronic device 130 determines whether the request for records is a request for all electronic medical records associated with the user 120 or whether only a subset of electronic medical records is needed. In some implementations, the request may be for electronic medical records of a certain type. For example, the request may be for electronic medical records related to orthopedic and muscular treatment. In other implementations, the request may be for records from designated providers. For example, the request may be for electronic medical records from a particular doctor and a particular hospital. In further implementations, the request may be for records from a particular time period. For example, the request may be for electronic medical records within the last ten years. Other implementations may enable a user to place other restrictions on a records request and may enable a user to place multiple restrictions on a record request.

The user electronic device 130 determines the location of the electronic medical records needed (330). For example, the user electronic device 130 may determine whether the user electronic device 130 stores the requested records locally on the user electronic device 130 or whether an electronic device at a remote location stores the requested records. The user electronic device 130 determines an electronic device that stores the requested records for each record requested. In some implementations, the user electronic device 130 may determine that the user electronic device 130 stores some of the requested records locally and each of the multiple record storage systems 140, 150, and 160 stores some of the requested records.

When the requested records are stored remotely in distributed storage, user electronic device 130 may determine the location of storage. In one example, user electronic device 130 may function as an address server that stores the addresses of the stored portions of a particular electronic medical record. The addresses of the stored portions may point to each individual storage locale on network 110 where a particular portion of the electronic medical record may be retrieved. In this example, the address may include a universal resource locator (URL), a stub, a hyperlink, or any exemplary location mechanism. In this example, the address information stored may include indirect address information. Specifically, the storage of certain portions of an electronic medical record may be determined by an address server, remote from user device 130. The address server may have assigned the storage of certain portions of an electronic medical record to one or more storage servers. The address server may have mapped the storage locations for each segment of the portions of the electronic medical record. As disclosed herein, when user electronic device 130 attempts to access portions of the electronic medical record, the user electronic device 130 may request a copy from the address server. The address server, in turn, may determine the whereabouts of the portions of the electronic medical record based on the mapping. Thereafter, the address server may fetch the requested copy on behalf of user electronic device 130 before relaying the copy back to user electronic device 130. In some instances, the address server may send the storage address back to user electronic device 130 so that user electronic device may update the storage mappings maintained on user electronic device 130. Once the mapping on user electronic device 130 has been updated, the user electronic device 130 may send a request directly to the storage server(s) where the portions are stored.

After determining the location of the records needed, the user electronic device 130 sends communications requesting records to electronic devices storing the requested records (340). For example, the user electronic device 130 may send electronic communications over network 110 to the multiple record storage systems 140, 150, and 160 requesting records. The electronic communication may identify the user 120 requesting the records, the user electronic device 130 requesting the records, the recipient 170, the recipient device 180 that may receive the records, the records that are requested and/or the restrictions placed on the records request.

The user electronic device 130 receives records sent from electronic devices storing the requested records in response to receiving a communication requesting records (350). For example, the user electronic device 130 may receive electronic records over network 110 from the multiple record storage systems 140, 150, and 160. In one implementation, the user electronic device 130 may also access records stored locally on the user electronic device. The user electronic device 130 may receive all of the requested records or may receive only a portion of the requested records. If the user electronic device 130 receives only a portion of the requested records, the user electronic device 130 may send communications requesting records again and/or may update a display to notify the user 120 that all of the requested records have not been received and may request further user input on how to proceed (e.g., whether to continue requesting records and/or whether to remove restrictions, such as restrictions on the provider of the records, in making subsequent records requests). The user electronic device 130 may transmit acknowledgements to the record storage system sending a particular electronic medical record when the user electronic device 130 receives the particular electronic medical record.

The user electronic device 130 renders a display of records information (360). For example, the user electronic device 130 may render a display of the records information on a display of the user electronic device 130 or may control a separate display device to render a display of the records information. The records information may include a listing of the records received, statistics associated with the records, and/or one or more of the electronic records received. In one implementation, the received records may be medical records and the user electronic device 130 may display a listing of the records. The listing of records may be organized by type, provider and/or date. The user 120 or the recipient 170 may browse the electronic records using the listing of records displayed on the user electronic device 130. For example, the user 120 or the recipient 170 may enter user input to the user electronic device 130 to display a medical record of interest.

In some implementations, the display may be transient and the assembled electronic medical record may not remain on user electronic device 130 for long. The duration of display, for example, may be configured by the user to be just long enough for a healthcare professional to see the contents. The duration of storage on the user's electronic device 130 may be controlled by a password token with a preset lifetime. The lifetime of the password token may be set by the patient on the user's electronic device 130. The temporary display may be applicable when the healthcare professional only need to verify information and does not need to retain the information. Example scenarios may include when the healthcare professional need to compare a newly acquired radiographic image with historically stored radiographic images stored over network 110 in a distributed storage system. Such distributed storage over network 110 with ubiquitous access may be known as cloud storage. In these scenarios, the persistence parameters may be set such that the electronic medical record assembled based on data segments from the cloud may not be printed to a physical copy. Screen capture programs may be turned off. Even scanning may be disabled temporarily.

In other implementations, the availability of the assembled electronic medical record may have a longer lifetime. For example, the assembled electronic medical record may be available for the duration of the patient's hospital stay. When the patient goes into an Intensive Care Unit (ICU), the assembled medical data may stay available throughout. When the patient stays at a rehabilitative facility, relevant electronic medical record may be accessible throughout the duration of the patient's stay.

The user electronic device 130 may, optionally, transfer the records to the recipient electronic device 180 (370). The user electronic device 130 may transfer the records to the recipient electronic device 180 over connection 190 or the network 110. As disclosed herein, the data transfer may take place over a wireless, a wired link, an RF link or an IR link. In some implementations, the data transfer may include a scanning mechanism. The recipient electronic device 180 may render a display of records information on a display of the recipient electronic device 180 or may control a separate display device to render a display of records information. The recipient electronic device 180 may store the received records locally on the recipient electronic device 180 or may store the received records on another device associated with the recipient 170 configured to store electronic records. In one implementation, the received records may be medical records for the user 120 and the recipient 170 may be a doctor providing treatment to the user 120. In this implementation, the doctor may use the recipient electronic device 180 to display the medical records of the user 120. The display of the recipient electronic device 180 may be better suited for displaying electronic medical records than the display of the user electronic device 130.

Figure 4:
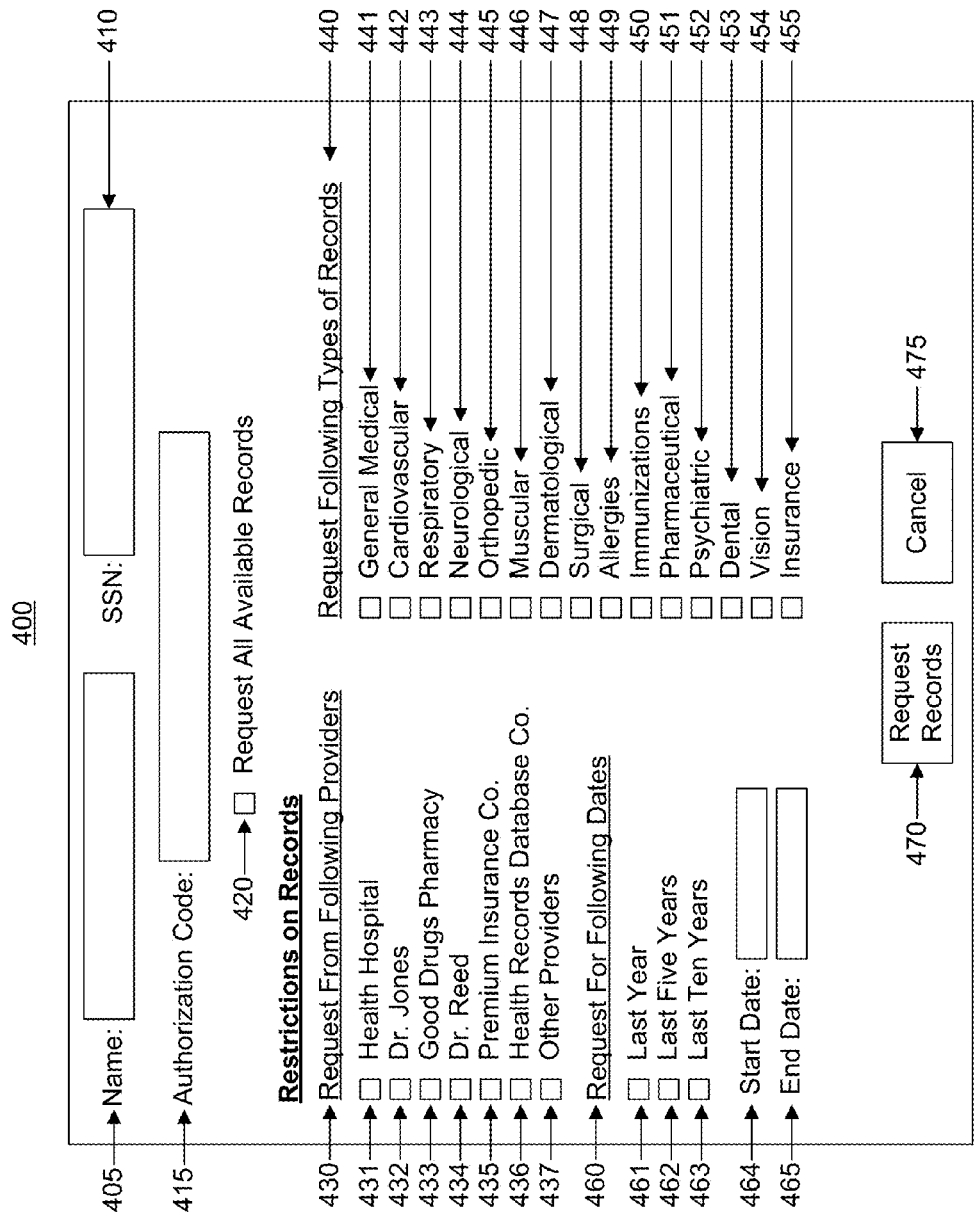
FIG. 4 illustrates an exemplary user interface for requesting records.

FIG. 4 illustrates an exemplary user interface 400 for requesting records. The user interface 400 may be presented to a user of a user electronic device requesting records. In one implementation, as shown, the user interface 400 may be used for requesting medical records associated with a user.

The user interface 400 includes a name text field 405, an identification text field 410, an authorization code text field 415, a request all available records check box 420, a restriction on providers portion 430, a restriction on type portion 440, a restriction on dates portion 460, a request records interface actionable item 470, and a cancel interface actionable item 475.

The name text field 405 identifies a name for the user of the user electronic device and enables the user to modify the name. The name of the user may be used in identifying records to retrieve and/or authentication processes.

The identification text field 410 identifies an identification number for the user of the user electronic device and enables the user to modify the identification number. The identification number of the user may be used in identifying records to retrieve and/or authentication processes. The identification number may be, for example, a social security number of the user.

The authorization code text field 415 identifies an authorization code for the user of the user electronic device and enables the user to modify the authorization code. The authorization code of the user may be used in authentication processes. For example, the user electronic device may provide the authorization code to a record storage provider and the record storage provider may only provide records to the user electronic device if the record storage provider receives a valid authorization code. The authorization code may timeout after an expiration date. After the expiration date, a new authorization code may be needed to obtain access the electronic medical record. As discussed herein, the authorization code also may be based on a digital biometric of the user, such as a fingerprint of the user.

The request all available records check box 420 enables a user to indicate that all available records for the user should be requested without restriction. When the request all available records check box 420 is checked, the restriction on providers portion 430, the restriction on type portion 440, and the restriction on dates portion 460 may be hidden or disabled.

The restriction on providers portion 430 includes check boxes 431-437 that enable a user to indicate that records should only be requested from the providers identified by the check boxes checked. The check boxes 431-437 may enable a user to restrict providers to specific doctors, hospitals, pharmacies, insurance companies, record storage companies, and/or any other providers. For example, the check box 431 may enable a user to restrict records to records from the provider Health Hospital, the check box 432 may enable a user to restrict records to records from the provider Dr. Jones, the check box 433 may enable a user to restrict records to records from the provider Good Drugs Pharmacy, the check box 434 may enable a user to restrict records to records from the provider Dr. Reed, the check box 435 may enable a user to restrict records to records from the provider Premium Insurance Co., the check box 436 may enable a user to restrict records to records from the provider Health Records Database Co., and the check box 437 may enable a user to restrict records to records from all other providers. The user interface 400 may include checkboxes for all providers from which the user has medical records, all providers from which the user has a threshold number of medical records, or a certain number of providers from which the user has the most medical records.

The restriction on type portion 440 includes check boxes 441-455 that enable a user to indicate that records should only be requested for the types identified by the check boxes checked. The check boxes 441-455 may enable a user to restrict providers to specific types of treatment, specific fields of treatment, and/or specific types of records. For example, the check box 441 may enable a user to restrict records to the type of General Medical, the check box 442 may enable a user to restrict records to the type of Cardiovascular, the check box 443 may enable a user to restrict records to the type of Respiratory, the check box 444 may enable a user to restrict records to the type of Neurological, the check box 445 may enable a user to restrict records to the type of Orthopedic, the check box 446 may enable a user to restrict records to the type of Muscular, the check box 447 may enable a user to restrict records to the type of Dermatological, the check box 448 may enable a user to restrict records to the type of Surgical, the check box 449 may enable a user to restrict records to the type of Allergies, the check box 450 may enable a user to restrict records to the type of Immunizations, the check box 451 may enable a user to restrict records to the type of Pharmaceutical, the check box 452 may enable a user to restrict records to the type of Psychiatric, the check box 453 may enable a user to restrict records to the type of Dental, the check box 454 may enable a user to restrict records to the type of Vision, the check box 455 may enable a user to restrict records to the type of Insurance records. The user interface 400 may include checkboxes for all types with which the user has medical records, all types with which the user has a threshold number of medical records, or a certain number of types with which the user has the most medical records.

The restriction on dates portion 460 includes check boxes 461-463, start date text field 464, and end date text field 465. The check boxes 461-463 enable a user to indicate that records should only be requested for a specific time period identified by the check box checked. The check boxes 461-463 enable a user to indicate that medical records should only be requested if the records are not older than a particular time. For example, the check box 461 may enable a user to restrict records to records dated within the last year, the check box 462 may enable a user to restrict records to records dated within the last five years, and the check box 463 may enable a user to restrict records to records dated within the last ten years. The check boxes 461-463 may be mutually exclusive and the start date text field 464 and the end date text field 465 may be hidden or disabled when one of the check boxes 461-463 is checked. The start date text field 464 and the end date text field 465 enable a user to specify a custom time period from which the user desires to request medical records. The start date text field 464 identifies a start date of a time period with which to request records and enables the user to modify the start date. The end date text field 465 identifies an end date of a time period with which to request records and enables the user to modify the end date.

The request records interface actionable item 470, when activated, initiates a record request operation using the information currently displayed by the user interface 400. The cancel interface actionable item 475, when activated, cancels the records request operation.

Figure 5:
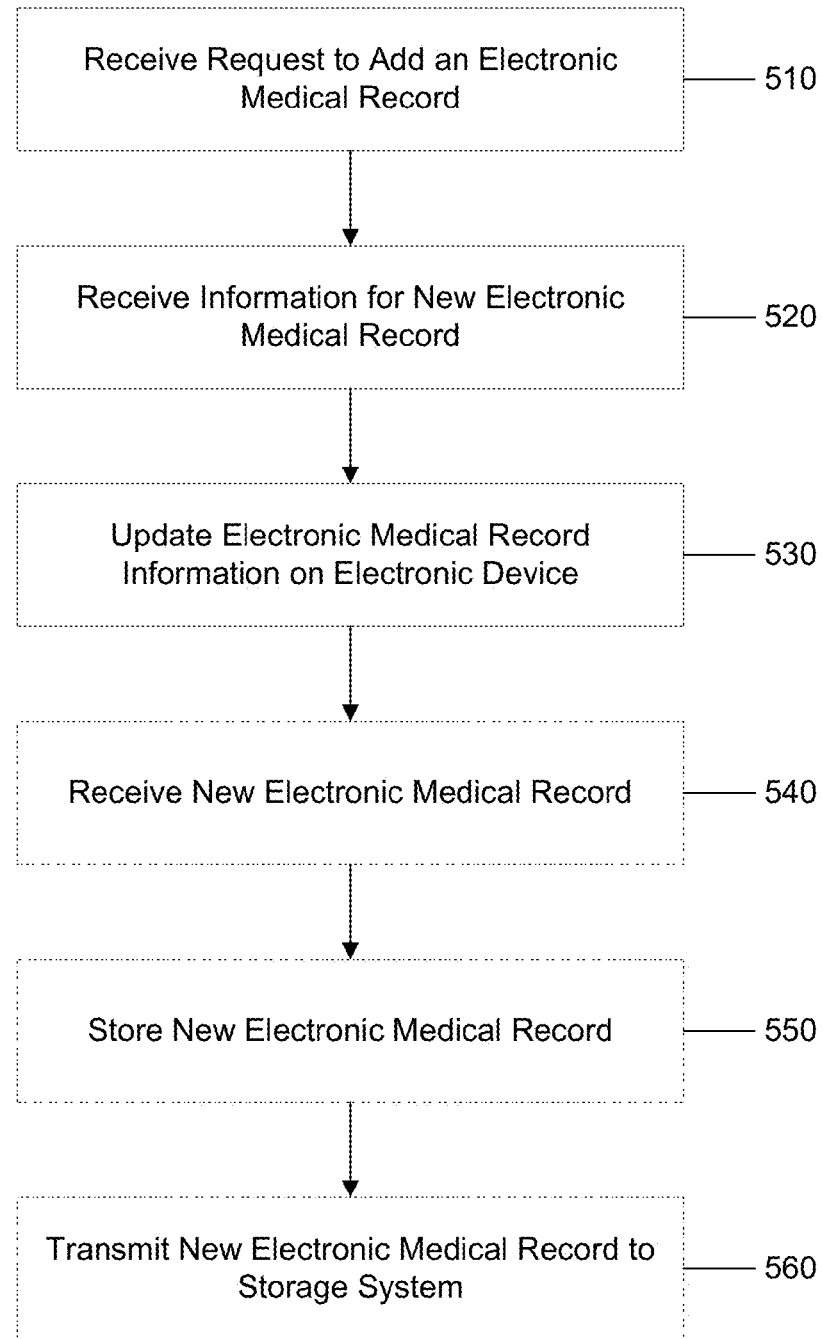
FIG. 5 is a flow chart of a process for adding a record.

FIG. 5 is a flow chart of a process 500 for adding an electronic medical record. For convenience, particular components described with respect to FIG. 1 are referenced as performing the process 500. However, similar methodologies may be applied in other implementations where different components are used to define the structure of the system, or where the functionality is distributed differently among the components shown by FIG. 1.

The user electronic device 130 receives a request to add an electronic medical record (510). For example, the user electronic device 130 may receive a request to add an electronic medical record associated with the user 120. In one implementation, the request to add a record may be received based on user input supplied to the user electronic device 130 by the user 120 or the recipient 170. In another implementation, the request to add a record may be received in an electronic communication over the connection 190 or the network 110. For example, the recipient electronic device 180 may send the user electronic device 130 a request to add a record over the connection 190 or one of the multiple record storage systems 140, 150, and 160 may send the user electronic device 130 a request to add a record over the network 110. In one implementation, the recipient 170 may use the recipient electronic device 180 to send a request to add a record to the user electronic device 130 over the connection 190. In this implementation, the record may include a medical record for the user 120 based on treatments and/or diagnosis provided by the recipient 170.

In some implementations, the request to add electronic medical record may be initiated during a medical study. For example, the patient may consent and participate in a medical study including, for example, a clinical trial for a drug, a medical device, or other healthcare products. By consent, the patient may submit medical data during the trial period so that the manufacturer may coalesce the data from a trial population (sometimes including a control population) and report to regulatory agencies. The data submission generally may be anonymous. In other words, the data may not include information identifying the particular patient. But the data may include information revealing certain characteristic of the patient (e.g., gender and age range). The data submitted may include information resulting from a treatment (either by the healthcare product or by a placebo). The treatment may be rendered in a double-blinded fashion. The information may include treatment efficacy and side effects, as recorded by scientific instruments that measure a particular physiologic parameter or image a particular region. These instruments also may be known as sensors. Such information may generally be termed as a particular biomarker. For diagnostic purposes, the biomarker may include, for example, glucose level, cholesterol level, blood pressure, body temperature, tumor size, vascularity of a mass, or viability of myocardial muscle. Additionally, subjective data, such as patient diary, may be reported in studies for such diseases as Alzheimer's disease, Parkinson's disease, or Wilson's disease. Some implementations may increase the scope of data available to regulatory agencies such as the Federal Drug Administration (FDA) during, for example, a phase III drug trial. The range of parameters that can be monitored has increased. So is the duration of the monitoring. The monitored data may be reported in confidentiality without comprising data security. Yet, the reported data may be authentic, with increased trustworthiness as coming from a patient without forgery or alteration.

As disclosed herein, in some implementations, electronic medical record may be reported to a central Patient Safety Organization (PSO). In some implementations, the PSO may serve as an intermediary to report data collected from patients participating in a medical study, for example, a safety study of a pharmaceutical product. The PSO may receive an electronic certificate to attest to the authenticity of the submitted data record. The electronic certificate may be used in one-factor or multi-factor authentication mechanism to prove an authenticity of the electronic medical record. The PSO may be a neutral party to the medical study. As such, the PSO may have less incentive to hold back from reporting negative or adverse effects. In comparison, such hold-back may be more prevalent when the electronic medical records are coming from the manufacturer running the medical study.

The user electronic device 130 receives new record information (520). For example, the user electronic device 130 may receive new record information for a record associated with the user 120. In one implementation, the new record information may be received based on user input supplied to the user electronic device 130 by the user 120 or the recipient 170. In another implementation, the new record information may be received in an electronic communication over the connection 190 or the network 110. For example, the recipient electronic device 180 may send the user electronic device 130 new record information over the connection 190 or one of the multiple record storage systems 140, 150, and 160 may send the user electronic device 130 new record information over the network 110. The new record information includes information related to the new record. For example, the new record information may include information identifying the new record, information identifying the location and/or the electronic device storing the new record, information related to the type, provider and/or date of the new record, and/or information identifying a user with which the record is associated. In one implementation, the new record information may include information related to a new medical record for the user 120. In this implementation, the new record information may indicate that the record is for the user 120, that the record relates to treatment received by the recipient 170, the date of the treatment, and the electronic device storing the new record (e.g., the recipient electronic device 180 or one of the multiple record storage systems 140, 150, and 160).

The user electronic device 130 updates record information (530). For example, the user electronic device 130 may update data related to records associated with the user 120. The updated data may include data sufficient to identify the new record and retrieve the new record if requested. In one implementation, the user electronic device 130 may update a database of medical record information associated with the user 120. In this implementation, the user electronic device may update a database stored locally on the user electronic device 130 and/or may update a database stored remotely from the user electronic device 130. The updated record information may indicate that a new medical record for the user is stored on a particular electronic device and may include information related to the type, the provider, and the date of the medical record.

The user electronic device 130 may, optionally, receive a new electronic record (540). For example, the user electronic device 130 may receive a new electronic record associated with the user 120. In one implementation, the new electronic record may be received based on user input supplied to the user electronic device 130 by the user 120 or the recipient 170. In another implementation, the new electronic record may be received in an electronic communication over the connection 190 or the network 110. For example, the recipient electronic device 180 may send the user electronic device 130 the new electronic record over the connection 190 or one of the multiple record storage systems 140, 150, and 160 may send the user electronic device 130 the new electronic record over the network 110. In one implementation, the recipient 170 may use the recipient electronic device 180 to send the new electronic record to the user electronic device 130 over the connection 190. In this implementation, the new electronic record may be a medical record for the user 120 based on treatments and/or diagnosis provided by the recipient 170.

The user electronic device 130 may, optionally, store the new electronic record (550). For example, the user electronic device 130 may store the new electronic record in local storage of the user electronic device 130. In one implementation, the new electronic record may be a medical record, the user electronic device 130 may maintain a database of medical records of the user 120, and the user electronic device 130 may update the database of medical records by storing the new electronic record.

As disclosed herein, the electronic medical record may be added to a database at a PSO. The database at the PSO may be shared among multiple data providers. The data sharing may rely on the chain of trust to authenticate the underlying electronic medical record, or portions thereof.

The addition of data may be part of a data reporting process during a medical study, for example, a clinical trial with hundreds or even thousands of participant patients, for which data addition and reporting may need to be synchronized.

In some implementations, electronic medical records may be supplemented by information collected from health related organizations. For example, recipient 170 may include health related organizations that the user has authorized to access specific electronic medical records of the user. Example organizations may even include social media sites and pharmacies.

In one example, electronic medical records, including fitness data, may be captured by mining social media channels such as blogs, facebook, twitter, or wechat. A user may post the fitness club participation data on social media channels, including data portals of the fitness club. In this example, data mining robot programs on the user electronic device 130 may search social media channels and capture such relevant healthcare information. The captured information may supplement an existing electronic medical record.

In another example, a patient may enter into a monitoring agreement with pharmacies or healthcare professionals. By way of illustration, pharmacies may offer discounted rates to attract patients to sign up for programs to monitor refill patterns. Likewise, healthcare professionals may offer discounts to patients in exchange for patients to sign up for a monitoring program that tracks follow-up visits, rehabilitation visits, readouts from sensors at home, etc. Under such monitoring programs, the user's electronic device 130 may generate electronic medical records based on the monitored refill pattern, follow-up visits, rehabilitation visits, and sensor readout. Such a medical record not only serves a reporting purpose, but also deters fraudulent insurance claim submissions (or insurance policy abuses).

The user electronic device 130 may, optionally, transmit the new electronic record to a database provider (560). For example, the user electronic device 130 may transmit the new electronic record to a database provider over the network 110 or the connection 190. In one implementation, the user electronic device 130 may receive a new electronic record from the recipient electronic device 180 over the connection 190 and may transmit the new electronic record to one of the multiple record storage systems 140, 150, and 160 over the network 110. In this implementation, the one of the multiple record storage systems 140, 150, and 160 stores the new electronic record and the user electronic device 130 may update record information stored on the user electronic device indicating that the new electronic record is stored on the one of the multiple record storage systems 140, 150, and 160.

Figure 6:
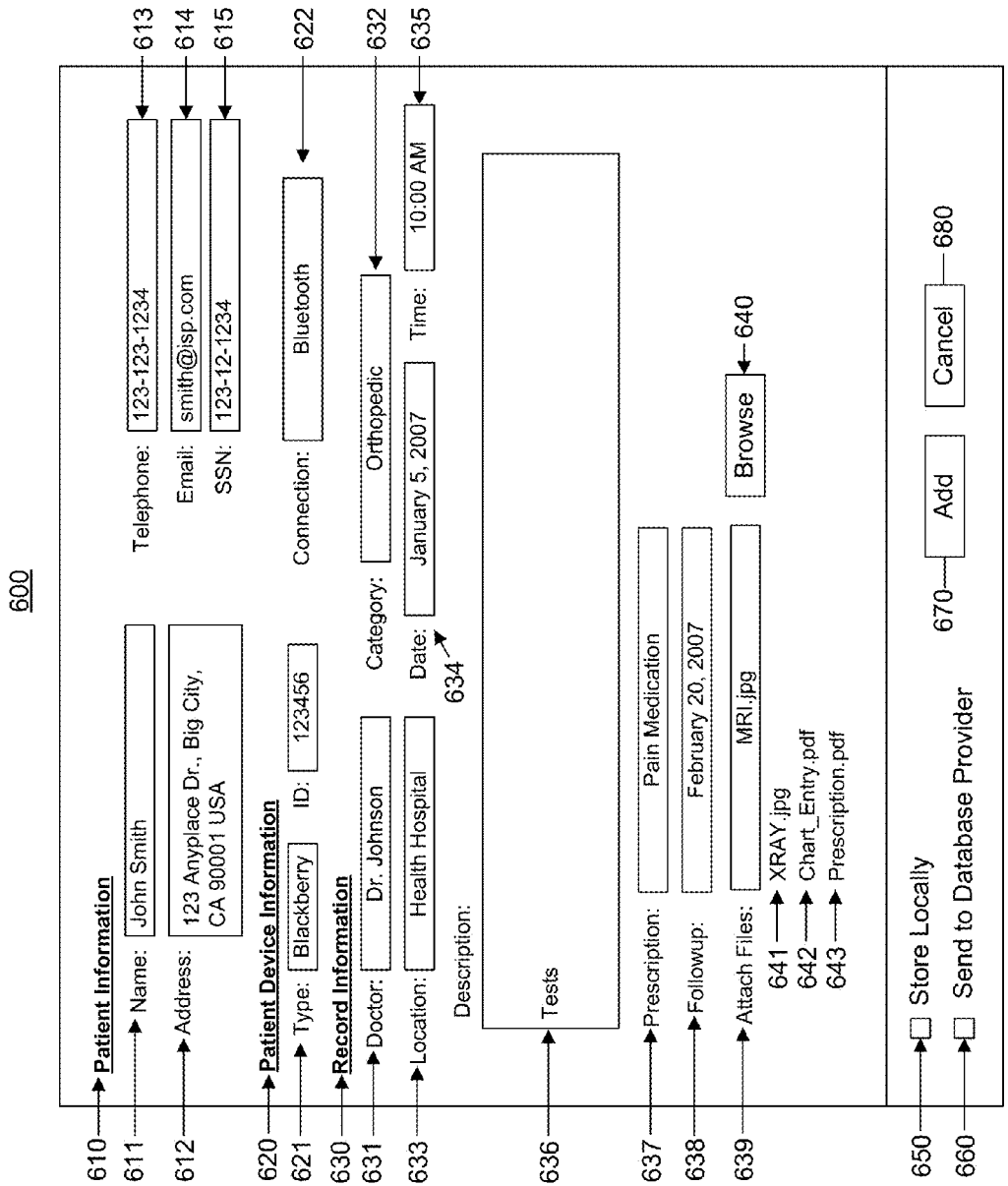
FIG. 6 illustrates an exemplary user interface for adding a record.

FIG. 6 illustrates an exemplary user interface 600 for adding a record. The user interface 600 may be presented to a user of a user electronic device or a recipient electronic device configured to add a record. In one implementation, as shown, the user interface 600 may be used for adding a medical record associated with a user.

The user interface 600 includes a patient information portion 610, a patient device information portion 620, a record information portion 630, a store locally check box 650, a send to database provider check box 660, an add record interface actionable item 670, and a cancel interface actionable item 680.

The patient information portion 610 includes a name text field 611, an address text field 612, a telephone number text field 613, an email text field 614, and an identification number text field 615. The name text field 611 identifies a name for a person associated with the record and enables the user to modify the name. The address text field 612 identifies an address for the person associated with the record and enables the user to modify the address. The telephone number text field 613 identifies a telephone number for the person associated with the record and enables the user to modify the telephone number. The email text field 614 identifies an email address for the person associated with the record and enables the user to modify the email address. The identification number text field 615 identifies an identification number for the person associated with the record and enables the user to modify the identification number. The identification number may be, for example, a social security number for the person associated with the record.

The patient device information portion 620 includes a device identification portion 621 and a connection portion 622. The device identification portion 621 includes a type text field and an identification number text field. The type text field identifies a type of the patient device and enables the user to modify the type. The identification number text field identifies an identification number of the patient device and enables the user to modify the identification number. The connection text field 622 identifies a connection type of the patient device and enables the user to modify the connection type of the patient device. The patient device information portion 620 enable a user to identify information associated with a patient device for use in sending the new record information or the new record to the patient device.

The record information portion 630 includes a doctor text field 631, a category text field 632, a location text field 633, a date text field 634, a time text field 635, a description text field 636, a prescription text field 637, a follow-up appointment text field 638, an attach files text field 639, and a browse interface actionable item 640. The doctor text field 631 identifies a name of a doctor associated with the new medical record and enables the user to modify the name of the doctor. The category text field 632 identifies a category associated with the new medical record and enables the user to modify the category. The location text field 633 identifies a location associated with the new medical record and enables the user to modify the location. The date text field 634 identifies a date associated with the new medical record and enables the user to modify the date. The time text field 635 identifies a time associated with the new medical record and enables the user to modify the time. The description text field 636 identifies a description associated with the new medical record and enables the user to modify the description. The prescription text field 637 identifies prescription associated with the new medical record and enables the user to modify the prescription. When a user enters a prescription in the prescription text field 637, a prescription may be automatically sent to a pharmacy when the medical record is added. The follow-up appointment text field 638 identifies a follow-up appointment associated with the new medical record and enables the user to modify the follow-up appointment. When a user enters a follow-up appointment in the follow-up appointment text field, a calendar entry for the follow-up appointment may be automatically entered in the doctor's calendar and the patient's calendar. The attach files text field 639 identifies a name of a file to attach associated with the new medical record and enables the user to modify the name of the file to attach. The attach file text field 639 may enable a user to attach other files to the medical record, such as images, other records, and/or other documents. For example, the user may attach patient image files (e.g., XRAY.jpg 641), chart entry images (e.g., Chart_Entry.pdf 642), and prescription image files (e.g., Prescription.pdf 643). The browse interface actionable item 640, when activated, may enable a user to browse a local directory for files to attach to the medical record.

The store locally check box 650 enables a user to indicate that the new medical record should be stored locally. For example, the store locally check box 650 may enable the user to indicate that the new medical record should be stored locally on the recipient electronic device with which the user is using to enter the new medical record information. In another example, the store locally check box 650 may enable the user to indicate that the new medical record should be stored locally on an electronic device associated with the doctor and/or location associated with the medical record.

The send to database provider check box 660 enables a user to indicate that the new medical record should be sent to a database provider to store the new medical record. For example, the send to database provider check box 660 may enable the user to indicate that the new medical record should be sent to a record storage system over a network for archival storage.

The add record interface actionable item 670, when activated, initiates an add record operation using the information currently displayed by the user interface 600. The cancel interface actionable item 680, when activated, cancels the add record operation.

Figure 7:
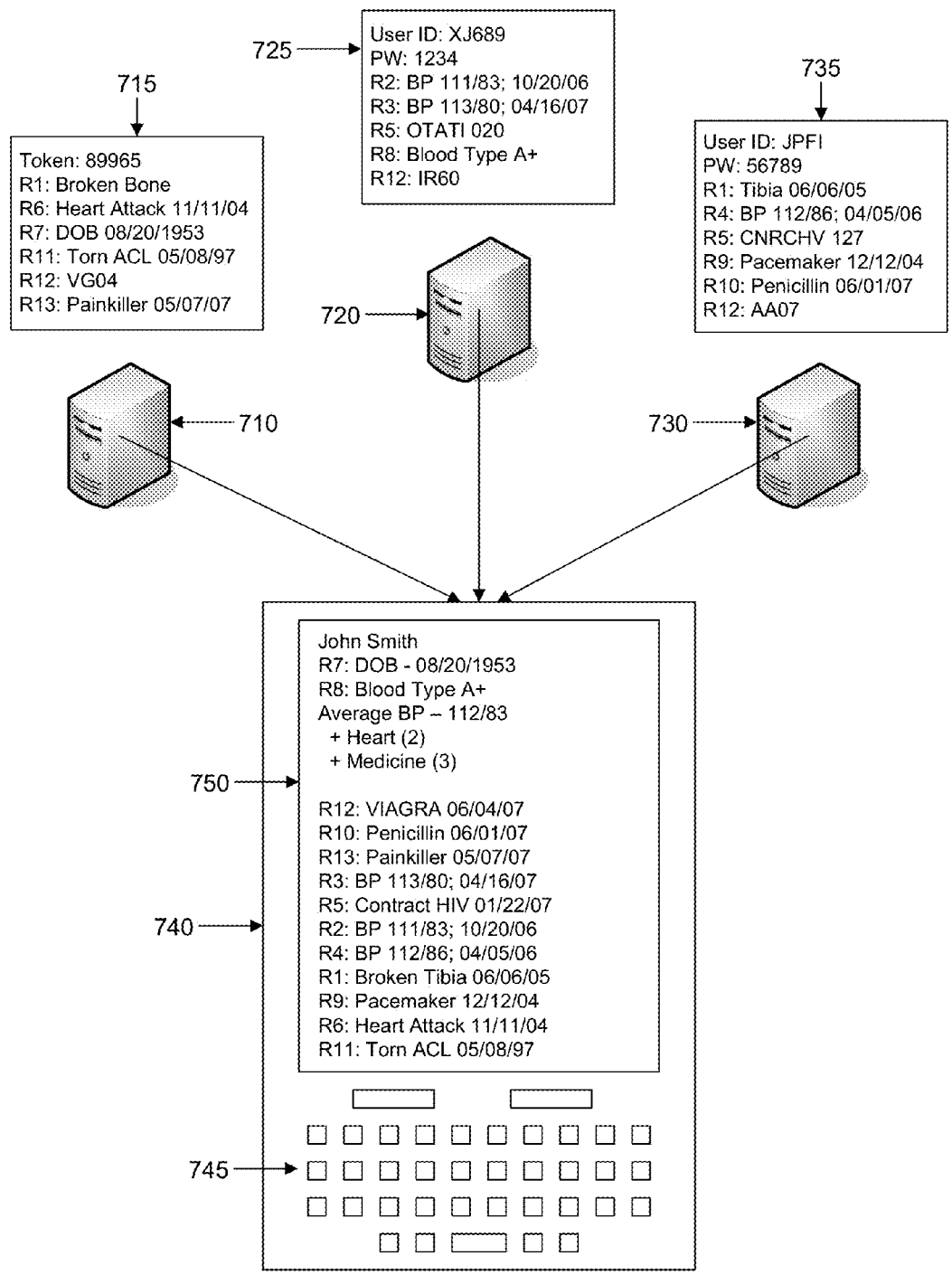
FIG. 7 is a contextual diagram illustrating anonymous medical record aggregation.

Referring to FIG. 7, medical record aggregation may be performed relatively anonymously. As shown, three (and perhaps many more or fewer) electronic medical records storage systems 710, 720, and 730 store electronic medical records for patients in a manner in which the electronic medical records for a particular patient and user identity information for the particular patient are disaggregated over the three electronic medical records storage systems 710, 720, and 730. Stated differently, a breach of one of the three electronic medical records storage systems 710, 720, and 730 does not enable identification of the particular patient by a breaching user, does not enable the breaching user to use identification and/or authentication information of the breach storage system to access the other storage systems, does not provide the breaching user with full access to the particular patient's entire set of medical records or even full information for particular records, and does not enable the breaching user to identify the other electronic medical records storage system in which the remaining medical record information for the particular patient is stored. Accordingly, using the electronic medical record aggregation techniques illustrated in FIG. 7, electronic medical record storage and aggregation may offer patients increased privacy and anonymity.

An electronic device 740 is used to aggregate and display medical records for a particular patient. The electronic device 740 serves as a secured proxy or conduit for accessing the disaggregated electronic medical records information stored in the electronic medical records storage systems 710, 720, and 730. In particular, the electronic device 740 may store information identifying the electronic medical records storage systems that store electronic medical records for the particular patient (e.g., electronic medical records storage systems 710, 720, and 730) and information needed to authenticate and retrieve electronic medical records for the particular patient from each of the electronic medical records storage systems. In some implementations, the electronic device 740 may communicate with another device over a network or through a direct connection to retrieve information needed to access the disaggregated electronic medical records information stored in the electronic medical records storage systems 710, 720, and 730.

The electronic device 740 includes an input unit 745 (e.g., a keypad, etc.) that enables a user to provide user input to the electronic device 740 and a display 750 that renders a display of electronic medical records information. The electronic device 740 includes a processor configured to control operations of the electronic device 740 and includes at least one computer-readable storage medium that stores instructions executed by the processor in performing the described processes and that stores information used by the electronic device 740 in serving as a secured proxy or conduit for accessing disaggregated electronic medical record information (e.g., identification information for electronic medical records storage systems, identification/authentication information for each of the electronic medical records storage systems, etc.). The electronic device 740 may be similar to the user electronic device 130 described above with respect to FIG. 1.

Referring to FIG. 7, a particular patient, John Smith, is associated with the electronic device 740. In this example, electronic medical records for John Smith are stored in three electronic medical records storage systems 710, 720, and 730 in a disaggregated manner and the electronic device 740 serves as a secured proxy that aggregates and displays the electronic medical records for John Smith. Electronic medical records storage systems 710, 720, and 730 may be similar to record storage system 140, 150, and 160 described above with respect to FIG. 1. Each of the three electronic medical records storage systems 710, 720, and 730 includes different identification information for John Smith and different authentication information required to obtain electronic medical records for John Smith.

Specifically, the electronic medical records storage system 710 stores electronic medical record information 715 for John Smith. As shown, the electronic medical records storage system 710 identifies John Smith and performs authentication of John Smith using a machine token. In this example, the machine token is labeled as Token: 89965. Accordingly, to retrieve electronic medical records for John Smith from the electronic medical records storage system 710, the electronic device 740 accesses (e.g., from electronic storage of the electronic device 740) the machine token 89965 and sends the machine token 89965 to the electronic medical records storage system 710. In response to receiving the machine token 89965, the electronic medical records storage system 710 authenticates the request as being from John Smith, accesses (e.g., from electronic storage of the electronic medical records storage system 710) electronic medical records associated with John Smith, and sends the accessed electronic medical records to the electronic device 740.

The electronic medical records storage system 720 stores electronic medical record information 725 for John Smith. As shown, the electronic medical records storage system 720 identifies John Smith as User ID: XJ689 and performs authentication of John Smith using the password "1234". Accordingly, to retrieve electronic medical records for John Smith from the electronic medical records storage system 720, the electronic device 740 accesses (e.g., from electronic storage of the electronic device 740) the user identification XJ689 and password "1234" information and sends the user identification XJ689 and password "1234" information to the electronic medical records storage system 720 in a request for medical records. In response to receiving the user identification XJ689 and password "1234" information, the electronic medical records storage system 720 authenticates the request as being from John Smith based on the user identification and password information, accesses (e.g., from electronic storage of the electronic medical records storage system 720) electronic medical records associated with John Smith, and sends the accessed electronic medical records to the electronic device 740.

The electronic medical records storage system 730 stores electronic medical record information 735 for John Smith. As shown, the electronic medical records storage system 730 identifies John Smith as User ID: JPFI and performs authentication of John Smith using the password "56789". To retrieve electronic medical records for John Smith from the electronic medical records storage system 730, the electronic device 740 uses techniques similar to those discussed above with respect to retrieving electronic medical records from the electronic medical records storage system 720, but uses the different identification information and password.

As such, when the electronic device 740 receives a request to access medical records (e.g., user input from the input unit 745 to access electronic medical records for John Smith), the electronic device 740 automatically, without human information, generates requests for electronic medical records from each of the three electronic medical records storage systems 710, 720, and 730 and aggregates the information to display to the user. More specifically, the electronic device 740 identifies each of the three electronic medical records storage systems 710, 720, and 730 as storing records for John Smith, identifies the differing identification/authentication information for each of the three electronic medical records storage systems 710, 720, and 730, and generates three separate requests for the three electronic medical records storage systems 710, 720, and 730 using the respective identification/authentication information. The electronic device 740 also may use different communication protocols or formats for sending and retrieving the electronic medical records for each of the three electronic medical records storage systems 710, 720, and 730.

In response to receiving a request from the electronic device 740, each of the three electronic medical records storage systems 710, 720, and 730 authenticates the request and, if the request is determined to be authentic, accesses and provides electronic medical records to the electronic device 740. For instance, in response to receiving a request from the electronic device 740 that includes the machine token 89965, the electronic medical records storage system 710 accesses the electronic medical records information 715 and sends electronic medical record information (e.g., records R1: Broken Bone, R6: Heart Attack Nov. 11, 2004, R7: DOB Aug. 20, 1953, R11: Torn ACL May 8, 1997, R12: VG04, and R13: Painkiller May 7, 2007) to the electronic device 740. In addition, in response to receiving a request from the electronic device 740 that includes the user ID XJ689 and the password "1234", the electronic medical records storage system 720 accesses the electronic medical records information 725 and sends electronic medical record information (e.g., records R2: BP 111/83; Oct. 20, 2006, R3: BP 113/80; Apr. 16, 2007, R5: OTATI 020, R8: Blood Type A+, and R12: IR60) to the electronic device 740. Furthermore, in response to receiving a request from the electronic device 740 that includes the user ID JPFI and the password "56789", the electronic medical records storage system 730 accesses the electronic medical records information 735 and sends electronic medical record information (e.g., records R1: Tibia Jun. 6, 2005, R4: BP 112/86; Apr. 5, 2006, R5: CNRCHV 127, R9: Pacemaker Dec. 12, 2004, R10: Penicillin Jun. 1, 2007, and R12: AA07) to the electronic device 740.

The electronic device 740 receives (e.g., over a network) the electronic medical record information from each of the three electronic medical records storage systems 710, 720, and 730 and aggregates the electronic medical record information into a complete set of medical records for John Smith. The electronic device 740 then renders a display of the aggregated electronic medical record information on the display 750.

In rendering the display, the electronic device 740 combines the electronic medical records information 715, 725, and 735 received from each of the three electronic medical records storage systems 710, 720, and 730, respectively. The electronic device 740 identifies records that include complete information (e.g., information for the records is received from only one source, although that information may or may not include all of the information typically associated with the record) and may display those records without further processing. As shown in FIG. 7, records R2 to R4, R6 to R11, and R13 are complete records and the electronic device 740 may combine those records into an aggregated/integrated display without additional processing.

For partial records (e.g., records in which information for the records is received from multiple sources), the electronic device 740 processes separate pieces received for each record and, in aggregating the records, generates a complete record based on the separate pieces. Partial records may be used for more sensitive information that warrants additional privacy protection. Because several pieces of information from several disaggregated sources are needed to generate a complete record, breach of the complete record may be more difficult.

For example, records R1, R5, and R12 represent partial records. As shown, record R1 includes information stored in the electronic medical records storage system 710 (e.g., R1: Broken Bone) and information stored in the electronic medical records storage system 730 (e.g., R1: Tibia Jun. 6, 2005). The information stored in both the electronic medical records storage systems 710 and 730 is needed to determine the complete medical record. In particular, the information stored in the electronic medical records storage system 710 indicates that the patient suffered a broken bone, but does not specify which bone was broken or when the bone was broken. The information stored in the electronic medical records storage system 730 indicates that the medical record is associated with the Tibia on the date Jun. 6, 2005, but does not specify what ailment or treatment associated with the Tibia occurred on Jun. 6, 2005. In combination, the electronic device 740 determines that the patient suffered a broken Tibia on Jun. 6, 2005 and may combine the partial records for display as "R1: Broken Tibia Jun. 6, 2005" in displaying the medical record R1.

Records R5 and R12 are examples of electronic medical records stored across multiple storage systems in which a particular process is needed to combine the partial information in generating a complete record. Specifically, record R5 includes information stored in the electronic medical records storage system 720 (e.g., R5: OTATI 020) and information stored in the electronic medical records storage system 730 (e.g., R5: CNRCHV 127). To generate the complete record R5, the electronic device 740 interleaves the characters included in the partial records received from the electronic medical records storage systems 720 and 730, starting with a character included in the electronic medical records storage system 730. In doing so, the electronic device 740 determines that the patient contracted HIV on Jan. 22, 2007 and may combine the partial records for display as "R5: Contract HIV Jan. 22, 2007" in displaying the medical record R5. Accordingly, to determine that the patient contracted HIV on Jan. 22, 2007, a breaching user would have to intercept both the information stored in the electronic medical records storage system 720 (e.g., R5: OTATI 020) and information stored in the electronic medical records storage system 730 (e.g., R5: CNRCHV 127), and know the particular process needed to combine the information. Breaching electronic medical record information stored in this manner may be difficult because intercepting one of the partial records would not convey intelligible information related to the record and, because the partial records are retrieved using different identification/authentication information and do not include information related to the combination process or other sources of the record, intercepting a single portion of the record would not lead a breaching user to find other portions of the record or the process needed to combine the disaggregated portions.

In another example, the record R12 includes information stored in the electronic medical records storage system 710 (e.g., R12: VG04), information stored in the electronic medical records storage system 720 (e.g., R12: IR60), and information stored in the electronic medical records storage system 730 (e.g., R12: AA07). To generate the complete record R12, the electronic device 740 interleaves the characters included in the partial records received from the electronic medical records storage systems 710, 720, and 730, starting with a character included in the electronic medical records storage system 710 through the electronic medical records storage system 730. In doing so, the electronic device 740 determines that the patient was issued a prescription for Viagra on Jun. 4, 2007 and may combine the partial records for display as "R12: VIAGRA Jun. 4, 2007" in displaying the medical record R12. Although particular examples of combining partial electronic medical records have been described, other processes and techniques for combining partial records to preserve anonymity may be used and/or combined with other techniques such as encryption.

In some implementations, the electronic device 740 renders a display based on the aggregated electronic medical records (e.g., complete records that were received as complete and partial records that have been combined to generate a complete record). In displaying the aggregated electronic medical records, the electronic device 740 may organize the display based on a variety of factors. For example, as shown in FIG. 7, the electronic device 740 may arrange the aggregated electronic medical records by date. In this example records R1 to R6 and R9 to R13 are arranged in reverse chronological order as R12, R10, R13, R3, R5, R2, R4, R1, R9, R6, and R11. Records R7 (Date of Birth) and R8 (Blood Type) are not associated with a date. Accordingly, records R7 and R8 may be displayed first or in a separate section used to distinguish dated medical records from undated medical records. A filter on the date of the electronic medical records may be used (e.g., electronic medical records older than a particular threshold, such as ten years, may be eliminated, or a particular date range may be defined in which to aggregate electronic medical records and only electronic medical records from the defined date range may be aggregated). Other rules may be used in organizing the display of electronic medical records, such as displaying electronic medical records based on a category and/or source of the electronic medical records.

The electronic device 740 may perform statistical processing on the electronic medical record data and display the results of the statistical processing. Displaying results of a statistical process performed on the electronic medical record data may make the electronic medical record data easier to digest and use by a medical services provider. In some implementations, the electronic device 740 may average electronic medical record data included in multiple electronic medical records received from one or multiple sources. As shown in FIG. 7, the electronic device 740 may compute an average blood pressure for a patient (e.g., John Smith) using the electronic device 740. The electronic device 740 may identify that records R2 to R4 include past blood pressure data and average the blood pressure data received in records R2 and R3 from the electronic medical records storage system 720 and record R4 from the electronic medical records storage system 730. As shown, the electronic device 740 determines and displays the average blood pressure as Average BP—112/83. Other statistical processes may be performed on the aggregated electronic medical records and other results may be determined and displayed by the electronic device 740.

As noted herein, the electronic device 740 may be similar to the user electronic device 130 described above with respect to FIG. 1A. In some implementations, the electronic device 740 may also include an ancillary date server, as illustrated in FIG. 1B. Electronic device 740 may also include a component to interface with a patient safety organization (PSO). The PSO interface component may collect patient data and report the data to a PSO. Such data may include, for example, heart rate summary data, respiration rate summary data, etc. Such data may be based on, for example, raw heart beat data collected in real-time. All data submitted may be stripped off patient-identifying information so that the submitted data is anonymous to preserve patient's privacy.

The PSO may include algorithmic implementations to present anonymous information to the health care provider that has contracted with the PSO. This anonymous information may not be provided to other parties. The anonymous information received from the PSO may be based on electronic medical records or portions of records of the patient who owns electronic device 740. The anonymous information received from the PSO could include aggregated information based on, for example, electronic medical records from all patients who receive service from the health care provider. As noted herein, the health care provider is in communication with the ancillary data server of electronic device 740.

In some instances, the information received from the PSO may include patient safety statistics on an anonymous basis, for example, during a drug trial. In other instances, the information received from the PSO may also include, for example, prescription patterns of a particular healthcare professional, or prescription-filling patterns at a given pharmacy store. In still other instances, the information received from the PSO may include prescription profiles of a particular patient. For example, an intelligent application on user electronic device 740 may communicate with, for example, electronic medical records storage systems 710, 720, and 730 to request such summary statistics. The summary statistics may include, for example, number of reported adverse effects for a pharmaceutical product, number of participating healthcare providers in an on-going drug trial, number of prescriptions written by a particular physician for a given pharmaceutical product. Likewise, more detailed statistics may become available to a pharmacy, a pharmaceutical manufacturer, an insurance company, or a regulatory agency. The more detailed statistics may include statistical distribution of a prescription pattern, confidence level of a given statistic metric, or even trend predictions for the prescription pattern of a particular pharmaceutical product.

As disclosed herein, electronic medical records, as retained at electronic medical records storage systems 710, 720, and 730 generally are stripped of patient-identifying information. Distributed storage of the electronic medical records in an anonymous form alleviates privacy concerns from individual patients as well as liability concerns from health care providers. In the meantime, distributed storage of electronic medical records for statistical analysis enables data mining of the aggregate electronic medical records to provide insightful information to stake holders including the individual patients, the healthcare providers, the insurance payers, as well as the regulatory agencies. The ability to extract value from the ocean of de-identified electronic medical records in distributed storage may enable a particular stake holder to better understand the related issues and make a more informed decision.

The PSO may serve as an intermediary to report data collected from patients participating in a medical study. The PSO may be a neutral party to the medical study. As such, the PSO may have less incentive to hold back from reporting negative or adverse effects. In comparison, such hold-back may be more prevalent when the electronic medical records are coming from the manufacturer running the medical study.

Indeed, the PSO is created to receive and process electronic medical records to generate feedback to remedy potential deficiencies or improve possible inefficiencies in current medical practice. The PSO may provide the analysis in a confidential manner. Participating healthcare professionals may not be penalized for any deficiencies or inefficiencies identified in the analysis as performed by the PSO.

Generally speaking, the submitting party of the electronic medical record may include healthcare providers, for example, hospitals, treating physicians, diagnostic labs, and rehabilitation facilities. Nonetheless, the benefits of having a separate PSO to aggregate and analyze anonymized electronic medical records may induce additional parties into sharing data. By way of illustration, a patient, or a delegate of the patient, may elect to participate in sharing electronic medical records of the patient. In one instance, a party in the capacity of a patient may conclude that the patient has nothing to lose in submitting the patient's electronic medical record in an anonymous manner. In other instances, the party in the capacity of the patient may have incentives to submit the electronic medical records of the patient anonymously. In such instances, under a quid-pro-quo arrangement, the party in the capacity of the patient may be economically enticed to share the electronic medical records of the patient anonymously in exchange for, for example, monetary compensation (however nominal, including receipt of coupons), or preferred access rights to results of analysis. When more parties share patients' electronic medical records, the pool size of data samples may increase, the overall quality of the raw data may improve, and the confidence of the statistical analysis may be enhanced. As stake holders start to reap the benefits of the shared data, the submitting parties may become more committed to more data sharing in the future.

In some instances, an application program on user electronic device 740 may be configured to submit the electronic medical record of the user anonymously. In one example, the application program may replace information in the electronic medical data that identifies the user with a random string, such as a hash. The random string may be used later to assemble segments of electronic medical data of the same user collected from distributed storage. The random string may also function as a key to download statistical analysis or trend prediction from, for example, data providers. In another example, the application program may intelligently decide which portions of the user's electronic medical records to be submitted. For instance, a template configuration may triage submission of electronic medical records. In one configuration, portions of the medical record considered as stigma may not be submitted. In another configuration, portions of the medical record that are overly voluminous may be condensed or coalesced before submission. Examples of voluminous portions may include: real-time recordings of the patient's cardiogram data, 3-dimensional imaging data, or 4-dimensional imaging data. By way of illustration, the cardiogram data may be trimmed to highlight a transitional trend, for example, under a stress test; voluminous imaging data may be condensed to reduce data size; longitudinal data may be coalesced to remove stationary entries showing no changes. In short, the reporting mechanism may be ad-hoc, yet consistent with the purpose and intent of PSOs to promote transparency without compromising privacy.

In other exemplary embodiments, the analysis performed on electronic medical records and any resulting data as described above can be shared with a number of other entities. In one instance, the data is shared with a caregiver. In another instance, the data is shared with a family member. In another instance, the data is shared with a health care provider or pharmacy, or school system. In these exemplary instances, the previously described process of sharing such data by authenticating the recipients and providing authentication information for the data being shared may be utilized. Some of this data may be shared anonymously. Some data may also be shared with identifying information as specified by the user.

The electronic device 740 also may group the aggregated electronic medical record data. The electronic device 740 may identify multiple electronic medical records that belong to a particular category. For instance, the electronic device 740 may group electronic medical records related to the heart in a category and also may group electronic medical records related to medicine the patient is currently taking and/or has taken in the past. The electronic device 740 may identify records R6 and R9 as being related to the heart and group records R6 and R9. The electronic device 740 also may identify records R10, R12, and R13 as being related to medicine and group records R10, R12, and R13. As shown in FIG. 7, the electronic device 740 may display the category of grouped electronic medical records along with the number of electronic medical records that have been grouped in the category (e.g., Heart (2) and Medicine (3)). Clicking on the displayed item associated with the group heart or the group medicine may display the electronic medical records that have been grouped into the particular category. Grouping records and displaying categories may enable a medical services provider to more quickly identify important/relevant electronic medical records without having to review a full set of electronic medical records. Clicking on a particular link may lead to other information related to the records (e.g., treatment or warning information related to the record), or more detailed information related to the record.

Although the user perceives the electronic medical records as all being stored on the electronic device 740, the electronic medical records are actually stored on the three electronic medical records storage systems 710, 720, and 730 in a disaggregated manner, and the interface provided by the electronic device is a virtual assemblage of those records. The electronic device 740 serves as a secure conduit configured to receive and display the disaggregated medical records.

Figure 8:
FIG. 8 is a flow chart of a process for anonymously aggregating medical records.

FIG. 8 is a flow chart of a process 800 for anonymously aggregating medical records. For convenience, particular components described with respect to FIG. 7 are referenced as performing the process 800. However, similar methodologies may be applied in other implementations where different components are used to define the structure of the system, or where the functionality is distributed differently among the components shown by FIG. 7.

The electronic device 740 initiates a process of aggregating electronic medical records associated with a patient (805). The process may be initiated in response to the patient providing user input to an electronic device associated with the patient. For instance, the patient may enter a command to display electronic medical records and process of aggregating electronic medical records may be triggered.

In response to initiation of the process of aggregating electronic medical records associated with the patient, the electronic device 740 identifies at least a first electronic medical records storage system and a second electronic medical records storage system that each store electronic medical records associated with the patient (810). The second electronic medical records storage system is different from the first electronic medical records storage system. The electronic device 740 may identify electronic medical records storage systems by accessing data stored at the electronic device 740 or may identify electronic medical records storage systems by communicating with another electronic device and receiving electronic records profile information for the patient. The first electronic medical records storage system and the second electronic medical records storage system may be unrelated and unaware of each other.

The electronic device 740 identifies first patient authentication information that enables retrieval of electronic medical records associated with the patient from the first electronic medical records storage system (815). The electronic device 740 may identify first patient authentication information that enables retrieval of electronic medical records associated with the patient from the first electronic medical records storage system by accessing data stored at the electronic device 740 or by communicating with another electronic device and receiving first patient authentication information. The electronic device may identify a first patient identifier and a first password for the first electronic medical records storage system. The combination of the first patient identifier and the first password enables retrieval of electronic medical records associated with the patient from the first electronic medical records storage system. The electronic device 740 also may identify a machine token for the first electronic medical records storage system.

The electronic device 740 identifies second patient authentication information that enables retrieval of electronic medical records associated with the patient from the second electronic medical records storage system (820). The second patient authentication information is different from the first patient authentication information. The electronic device 740 may identify second patient authentication information that enables retrieval of electronic medical records associated with the patient from the second electronic medical records storage system by accessing data stored at the electronic device 740 or by communicating with another electronic device and receiving second patient authentication information. The electronic device 740 may identify a second patient identifier and a second password for the second electronic medical records storage system. The combination of the second patient identifier and the second password enables retrieval of electronic medical records associated with the patient from the second electronic medical records storage system. A first patient identifier for the first electronic medical records storage system may be different than the second patient identifier for the second electronic medical records storage system and a first password for the first electronic medical records storage system may be different than the second password for the second electronic medical records storage system. The electronic device 740 may identify a machine token for the second electronic medical records storage system (which may be a second machine token that is different than a first machine token for the first electronic medical records storage system).

The electronic device 740 generates a first request for medical records using the first patient authentication information and generates a second request for medical records using the second patient authentication information (825). The electronic device 740 may generate first and second requests by including the first and second authentication information in electronic communications to be sent to the first and second electronic medical records storage systems, respectively. The electronic device 740 may generate the first and second request using different protocols, formats, and/or encryption techniques suitable for the first and second electronic medical records storage systems, respectively. The electronic device 740 may store information needed to generate the requests with the information and format needed for the electronic medical records storage systems. In some examples, the electronic device 740 generates a first request that includes a first patient identifier and a first password, and generates a second request that includes a second patient identifier and a second password. In other examples, the electronic device 740 generates a first request that includes a machine token for the first electronic medical records storage system, and generates a second request that includes a patient identifier and a password for the second electronic medical records storage system. The first and second requests may include any combination of authentication information, such as machine tokens, passwords, identifiers, encryption techniques, encoding, etc.

The electronic device 740 transmits the first request to the first electronic medical records storage system and transmits the second request to the second electronic medical records storage system (830). For instance, the electronic device 740 sends the first and second requests to the first and second electronic medical records storage systems as electronic communications over a network. The first and second requests may be transmitted at the same time or at different times.

The electronic device 740 receives, from the first electronic medical records storage system, a first response including at least a first portion of one or more electronic medical records for the patient stored at the first electronic medical records storage system (835). The first response is sent from the first electronic medical records storage system in response to the first electronic medical records storage system receiving the first request and authenticating the first request based on the first patient authentication information.

The electronic device 740 receives, from the second electronic medical records storage system, a second response including at least a second portion of one or more electronic medical records for the patient stored at the second electronic medical records storage system (840). The second response is sent from the second electronic medical records storage system in response to the second electronic medical records storage system receiving the second request and authenticating the second request based on the second patient authentication information. The first and second responses may not include identifying information associated with the patient and also may not include information identifying any of the other electronic medical records storage system. Limiting information in the first and second response to the specific electronic medical records storage system sending the response may promote anonymity and privacy in electronic medical records because breach of a single storage system or response does not lead to information that enables breach of the entire set of electronic medical records.

The electronic device 740 generates a set of electronic medical records associated with the patient by combining the first portion of one or more electronic medical records for the patient included in the first response with the second portion of one or more electronic medical records for the patient included in the second response (845). In some implementations, the electronic device 740 receives a first response that includes a first portion of a first electronic medical record for the patient stored at the first electronic medical records storage system, and receives a second response that includes a second portion of the first electronic medical record for the patient stored at the second electronic medical records storage system. In these implementations, the electronic device 740 combines the first portion of the first electronic medical record with the second portion of the first electronic medical record to generate a complete first electronic medical record. Once the electronic devices 740 has generated complete electronic medical records from partial records received (or received complete electronic medical records), the electronic device 740 combines the complete records into a set of electronic medical records for the patient. The electronic device 740 may organize the electronic medical records in the set by date, by category, or by another type of classification technique. The electronic device 740 also may filter the electronic medical records prior combining the electronic medical records into the set based on user-defined filter criteria. In some examples, the electronic device 740 may detect inconsistencies or redundancies in the aggregated electronic medical records. In these examples, the electronic device 740 may automatically resolve/correct the inconsistencies and/or redundancies or may flag the inconsistencies and/or redundancies to alert a viewer of the electronic medical records.

The electronic device 740 enables display of the generated set of electronic medical records associated with the patient (850). The electronic device 740 may display a virtual assemblage of the electronic medical records as a single file. The electronic device 740 also may perform statistical processing or grouping on the received electronic medical records prior to displaying electronic medical record information. The electronic device 740 further may transmit the electronic medical record information to another device and the other device may display the electronic medical record information. Transmitting the electronic medical record information to another device for display may be beneficial when the other device has a larger or otherwise more suited display for viewing electronic medical records and/or any images (e.g., x-rays) associated with the electronic medical records.

In some implementations, identifying at least the first electronic medical records storage system and the second electronic medical records storage system, identifying first patient authentication information, identifying second patient authentication information, generating the first request, generating the second request, transmitting the first request, transmitting the second request, receiving the first response, receiving the second response, generating the set of electronic medical records, and enabling display of the generated set of electronic medical records occur automatically, without human intervention, in response to initiation of the process of aggregating electronic medical records associated with the patient. Further, both the first request and the first response may not include information that identifies the second electronic medical records storage system such that interception of the first request and the first response does not lead to identification of electronic medical records stored in the second electronic medical records storage system. In addition, both the second request and the second response may not include information that identifies the first electronic medical records storage system.

Figure 9:
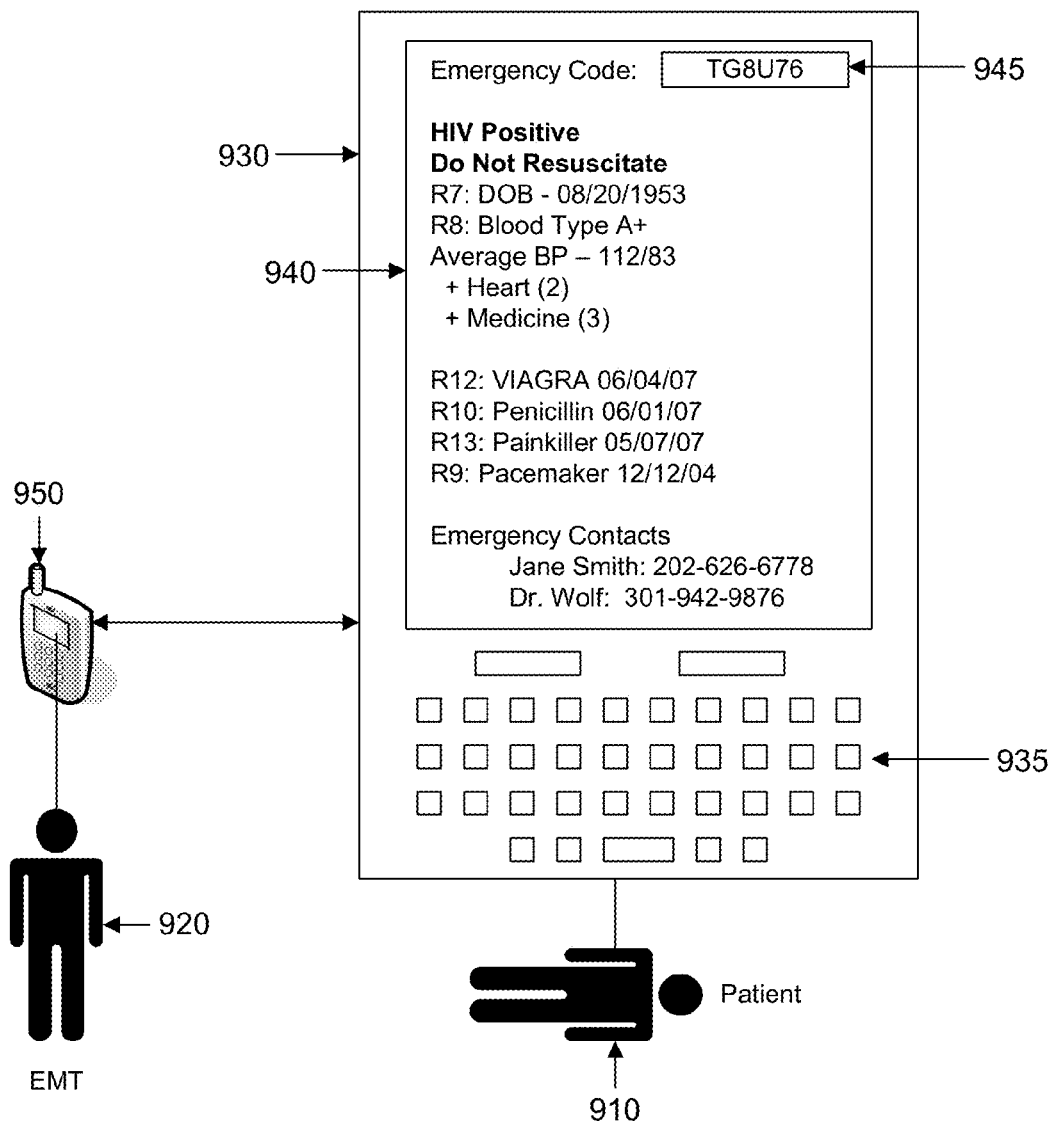
FIG. 9 is a contextual diagram illustrating emergency service provider access to medical records.

Referring to FIG. 9, an emergency services provider 920 may be provided with access to medical records associated with a patient 910 the emergency services provider 920 is treating. The emergency services provider 920 uses a patient electronic device 930 that belongs to the patient 910 to aggregate electronic medical records associated with the patient 910 and render a display of the aggregated electronic medical records. The patient electronic device 930 includes an input unit 935 (e.g., a keypad, etc.) that enables a user to provide user input to the patient electronic device 930 and a display 940 that renders a display of electronic medical records information. The patient electronic device 930 includes a processor configured to control operations of the patient electronic device 930 and includes at least one computer-readable storage medium that stores instructions executed by the processor in performing the described processes and that stores information used by the patient electronic device 930 in serving as a secured proxy or conduit for accessing disaggregated electronic medical record information (e.g., identification information for electronic medical records storage systems, identification/authentication information for each of the electronic medical records storage systems, etc.). The patient electronic device 930 may be similar to the user electronic device 130 described above with respect to FIG. 1 and the electronic device 740 described above with respect to FIG. 7.

The patient electronic device 930 may be configured to aggregate electronic medical records for the patient 910 using techniques similar to those described above. The patient electronic device 930 further may be configured to authenticate emergency services providers (e.g., emergency services provider 920) and aggregate electronic medical records associated with the patient 910 to display to the emergency services provider 920. In response to authenticating an emergency services provider, the patient electronic device 930 may aggregate electronic medical records as if the patient 910 had made the aggregation request. In one example, user electronic device 130 may allow authorized emergency service provider 920 to access user electronic device 130 when, for example, user 120 has been rendered unconscious in an emergency situation. In this example, user 120 may have delegated, for example, by default, emergency service provider 920 to act on behalf of user 120 in case user 120 is incapacitated in an emergency.

In authenticating the emergency services provider 920, the patient electronic device 930 may request the emergency services provider 920 to enter a password or passcode. For instance, the patient electronic device 930 may render a display of an input control 945 on the display 940, and the emergency services provider 920 may enter a password or passcode using the input control 945. The patient electronic device 930 may compare the entered password to a valid password and determine whether to authenticate the emergency service provider 920 based on whether the comparison reveals that the entered password matches a valid password.

In some implementations, the valid password may be a single, valid password known to all emergency services providers. The valid password also may be provider-specific such that each licensed emergency services provider has a unique password used in authentication. The patient electronic device 930 may require the emergency service provider 920 to enter identification information (e.g., an employee ID, a badge number, name, etc.) prior to authentication. Requiring entry of identification information may enable tracking of emergency service provider access to electronic medical records of other patients. A tracking system may track emergency service provider access to electronic medical records to identify emergency service providers that are accessing electronic medical records inappropriately or identify when emergency service provider access credentials have been comprised (e.g., a particular emergency services provider is making an undue number of medical records access requests or requesting electronic medical records for a patient that the emergency services provider is not treating).

The patient electronic device 930 may store emergency services provider authentication information and perform emergency services provider authentication based on the stored emergency services provider authentication information. In some examples, the patient electronic device 930 may communicate with a centralized emergency services provider's authentication electronic device to perform authentication. The patient electronic device 930 may receive authentication information (e.g., valid password(s)) from the centralized emergency services providers' authentication electronic device and perform emergency services provider authentication based on the received emergency services provider authentication information. The patient electronic device 930 also may provide authentication information inputted by the emergency services provider 920 to the centralized emergency services providers authentication electronic device, the centralized emergency services providers authentication electronic device may authenticate the inputted authentication information, and the centralized emergency services providers authentication electronic device may report the results of authentication to the patient electronic device 930. The centralized emergency services providers' authentication electronic device may track emergency service provider access to electronic medical records, generate reports, and send warnings when suspicious electronic medical records access occurs.

A senior citizen may have signed a medical power of attorney designating a caregiver so that the caregiver will make health care decisions on behalf of the senior citizen should the senior citizen become unable to make such decisions. When the senior citizen is incapacitated, the caregiver may act quickly on behalf of the senior citizen. To do so, the caregiver may need access to medical records of the senior citizen so that healthcare professionals, like treating physicians, may make informed decisions in rendering treatment. To enable the caregiver to access medical records on behalf of the senior citizen, the caregiver may be given limited access commensurate with the scope of the medical power of attorney. The caregiver may be granted such access to the medical records of the senior citizen stored in fragments in distributed locations. The caregiver may also be given corresponding access to a mobile device of the senior citizen so that the caregiver may access medical records of the senior citizen from the mobile device of the senior citizen. In this scenario, the senior citizen may have authorized the caregiver access to the mobile device of the senior citizen. The access may be limited in accordance with the scope of the medical power of attorney. What is more, the caregiver may submit requests for electronic medical records from the senior citizen's mobile device according to the medical power of attorney. The submitted request may identify the caregiver as the data requester, rather than the senior citizen. In cases where the caregiver is a partnership or a co-op facility, such as a senior living community, the medical power of attorney may extend to designated members of the partnership or co-op facility. In other cases, if the caregiver is a corporation, the medical power of attorney may extend to its subsidiaries, affiliates, or even parent companies. In special cases, the medical power of attorney may also exist in accordance with an alter ego of the corporation.

In a similar vein, a child may have the child's health care decisions designated to a custodian. In most cases, the custodian is one of the parents. In some cases, the custodian may include another family member, or even a third party. The example situations are not limited to divorce proceedings in which a child may be at the custody of a family member. By way of example, the child may be at an intramural sports team, community sports or tournament. The sport at issue may not be limited to recreational sports and may have an element of competition, such as, for example, a hockey game, a baseball game, swimming lessons. In fact, some intramural sports may require each participant to sign a medical power of attorney designating a person, such as the coaching staff of the school, to make healthcare decisions if the participant is rendered unconscious by an accident during the game. In another example, the school that the child attends may need access to the child's electronic medical record. Example situations may include when the child is on a sport team organized by the school, when the child goes on a field trip organized by the school, or when the child participates in daily school routines. In these example situations, if the child experiences an injury or accident, designated school personnel may act on behalf of the child in seeking medical attention.

In the above examples, the designated person may have limited access to the electronic medical record of the participant (e.g., a minor) during an accident that renders the child unconscious and the child's custodian is not present. Generally, the situations necessitating a designated person to serve as caregiver during emergency also may include participating in a sports club, a gym, a yachting event, etc. The scope of the access to data is limited in accordance with the medical power of attorney. To obtain the access, the designated person may be authenticated based on, for example, an authentication credential. As disclosed herein, the authentication credential may include a password token issued by the participant (including the custodian of the child). The authentication credential may also include hardware token unique to the designated person. In one example, the request for medical record data may be submitted from the participant's mobile device. In this example, the request may be submitted along with information indicating that the request is being submitted by the designated person on behalf of the participant. In another example, the request for medical record data may be submitted from the designated person's computing device. The designated person may have been pre-registered by the participant as one authorized party on a list of pre-approved parties. Hence, some implementations disclosed herein may establish a chain of delegation, for example, to custodian, to a designated person in times of emergency. In some implementations, an application program on user electronic device 130 may perform the delegation tasks. For example, the application program may incorporate an expert system configuration to determine the scope of medical information to be disclosed to the delegate. The determination may be based on specific criteria set beforehand and driven by events. For instance, the application program may be configured to disclose more information to a delegate during a scheduled sports event than during school routines. The disclosure may be determined based on the capacity of the delegate making the request. When the request is being made by the school coach during a scheduled sport team event, the scope of disclosure may be comprehensive, including, for example, physiologic parameters, or past medical treatments. However, when the request comes from the school principal during routine hours, the scope of disclosure may be limited to summary level information of the child, such as, for example, calories consumed, activities performed.

The valid authentication information (e.g., the valid password) may change over time (e.g., a new password may be issued daily). For example, each emergency service provider may receive a new password each day that the emergency service provider works. The new password may be received using secure, electronic communication mechanisms or may be posted in an area in which only authorized emergency services providers are intended to be present (e.g., a back room of a police office). The patient electronic device 930 may periodically receive updated authentication information (e.g., passwords, tokens, etc.) for licensed/authorized emergency services providers or may request and receive authentication information (e.g., passwords, tokens, etc.) for a particular emergency services provider in response to the particular emergency services provider requesting electronic medical records using another user's device. Changing the authentication information (e.g., valid password) may reduce the risks associated with potential breach of emergency service provider authentication information and limit inappropriate access to electronic medical records.

The emergency services provider 920 also may need to perform hardware authentication to access electronic medical records associated with the patient 910 using the patient electronic device 930. The hardware authentication may be additional to, or an alternative to, the password-based authentication described above. The hardware authentication may require the emergency services provider 920 to physically possess a particular hardware device to be authenticated as a licensed emergency services provider. For instance, the particular hardware device may be a hardware key or dongle that the emergency services provider physically connects to the patient electronic device for authentication.

In some implementations, the hardware device used for hardware authentication may electronically connect to the patient electronic device 930 over a wireless connection. For example, as shown in FIG. 9, the hardware device may be a wireless communication device 950 that the emergency services provider 920 uses to perform a hardware authentication operation. In this example, the wireless communication device 950 may exchange a predefined series of communications with the patient electronic device 930 and the patient electronic device 930 authenticates the emergency service provider based on the exchanged communications (e.g., alone or by communicating with another centralized authentication device). The communications that are exchanged by the wireless communication device 950 and that are needed for authentication may be changed over time as discussed above with the password authentication. Use of the wireless communications device 950 (or another hardware authentication device) also may be tracked as discussed above. The particular hardware device only may be issued to licensed emergency services providers and may be under the control of emergency services agencies such that the emergency services agencies.

In response to authenticating the emergency services provider 920, the patient electronic device 930 aggregates electronic medical records associated with the patient 910 and renders a display of the aggregated electronic medical records. The process of aggregating and displaying electronic medical records associated with the patient 910 may be performed using techniques similar to those discussed above with respect to FIG. 7.

In some implementations, access to all of the electronic medical records for the patient 910 may not be given to the emergency services provider 920. In these implementations, the access given to the emergency services provider 920 may include electronic medical records beneficial to providing emergency medical treatment and exclude electronic medical records that are irrelevant or of lesser importance to emergency medical treatment. Accordingly, the emergency services provider 920 may receive fewer electronic medical records than the patient 910 (e.g., as shown in the difference in electronic medical records displayed in FIG. 7 and electronic medical records displayed in FIG. 9). The patient 910 may define the level of access to provider to the emergency services provider 920 and the type of medical records (or which records) to provide to the emergency service provider 920.

In further implementations, different levels of access may be provided to emergency services providers with different credentials. For instance, an ambulance driver may be provided with fewer records than an emergency room doctor treating the patient 910 and the emergency room doctor may be provided with fewer records than a surgeon performing emergency surgery on the patient 910. The level of access (e.g., number and type of records) may be tailored to the type of service being provided by the emergency services provider. The level of access may be defined based on preferences of the patient, may be defined automatically based on authentication information received from the emergency services provider, or may be defined based on which records are requested by the emergency services provider.

In some examples, additional information may be provided to the emergency services provider 920 that is not provided when the patient 910 requests electronic medical records. In these examples, the additional information may include emergency contact information and living will information (e.g., the patient's preference as to whether the patient wishes to be resuscitated). Information also may be provided in a different format to the emergency services provider 920 than the patient 910. For instance, the patient electronic device 930 may display information that may pose a risk to the emergency services provider 920 in a different section or in a highlighted manner (e.g., highlight HIV Positive).

In some implementations, the patient electronic device 930 may send electronic medical records to a hospital or other emergency services provider in response to an initial emergency service provider authentication and records aggregation operation. In these implementations, in response to the emergency services provider 920 being authenticated to the patient electronic device 930, the patient electronic device 930 may automatically send (or control another device to send) electronic medical records to a hospital or doctor's office to which the patient 910 is being taken for further treatment. The electronic medical records sent to the hospital or doctor's office may include the same electronic medical records aggregated and displayed to the emergency services provider 920 or may include more or fewer electronic medical records. The hospital or doctor's office may be determined based on user input provided to the patient electronic device 930 by the emergency services provider 920 or may be automatically determined based on information known about the emergency service provider 920 (e.g., a hospital for which the emergency services provider 920 works) or information known about the patient 910 (e.g., a family doctor used by the patient 910). Providing electronic medical records to the hospital or doctor's office in advance of the patient 910 arriving may improve the emergency medical treatment because emergency services providers at the hospital or doctor's office may have some time to review the medical records prior to the patient 910 arriving.

Input from the patient 910 also may be needed to authenticate the emergency services provider 920. For example, a biometric input (e.g., a fingerprint scan or retinal scan) of the patient 910 may be needed to authenticate the emergency services provider 920. The biometric input may confirm that the patient 910 is nearby the emergency services provider 920 attempting to access the electronic medical records and also is a type of input that the patient 910 may provide when the patient is unconscious or otherwise incapacitated when being treated by the emergency services provider 920.

Figure 10:
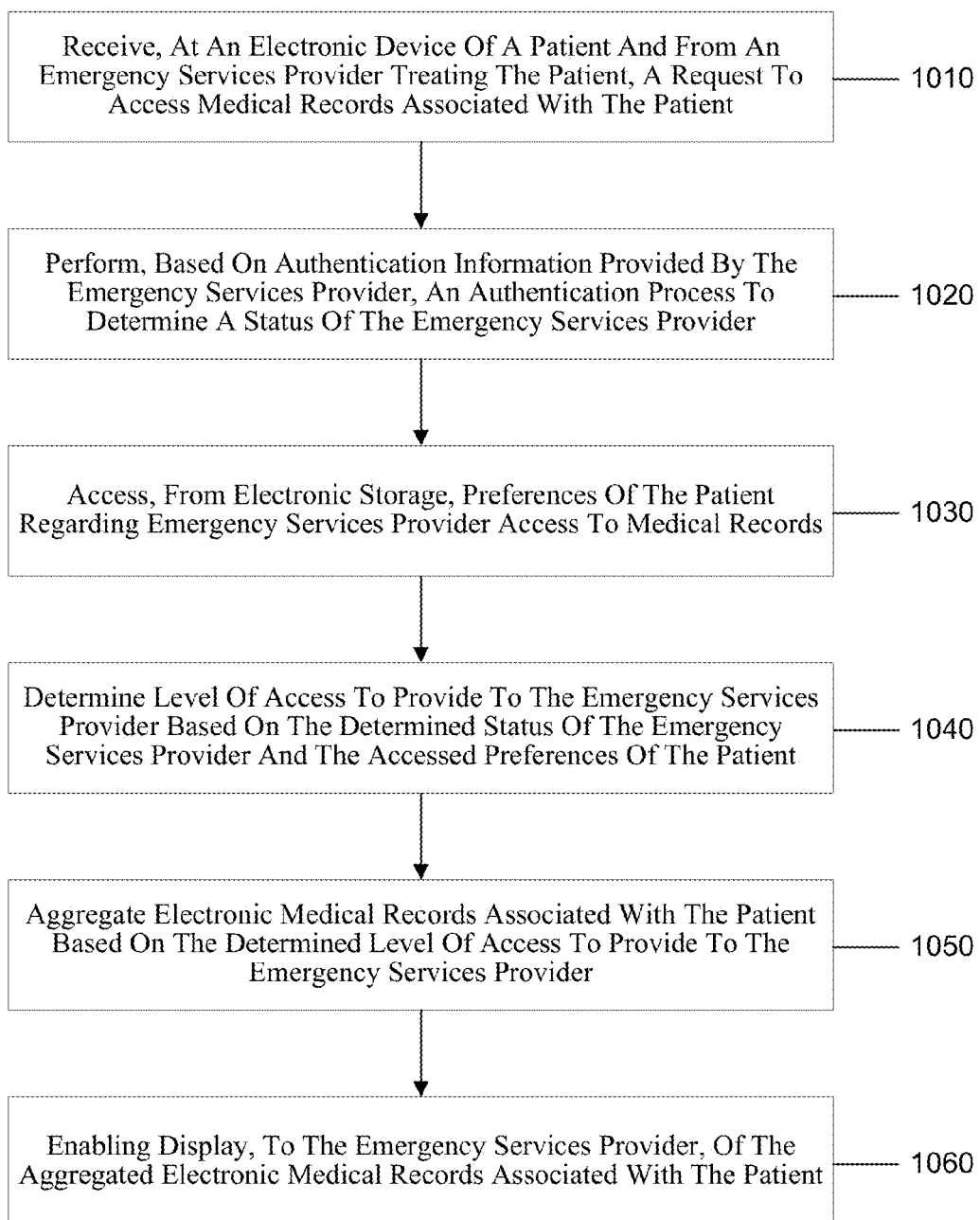
FIG. 10 is a flow chart of a process for enabling an emergency service provider to access medical records of a patient.

FIG. 10 is a flow chart of a process 1000 for enabling an emergency service provider to access medical records of a patient. For convenience, particular components described with respect to FIG. 9 are referenced as performing the process 1000. However, similar methodologies may be applied in other implementations where different components are used to define the structure of the system, or where the functionality is distributed differently among the components shown by FIG. 9.

The patient electronic device 930 receives, from an emergency services provider 920 treating a patient 910 to which the patient electronic device 930 belongs, a request to access medical records associated with the patient 910 (1010). The patient electronic device 930 may receive the request to access medical records associated with the patient 910 based on user input provided to the patient electronic device 930 by the emergency services provider 920 or may receive the request to access medical records associated with the patient 910 in an electronic communication sent from the wireless communication device 950.

In response to receiving the request from the emergency services provider 920, the patient electronic device 930 performs, based on authentication information provided to the electronic device by the emergency services provider 920, an authentication process on the emergency services provider 920 to determine a status of the emergency services provider 920 (1020). For instance, the patient electronic device may perform a two stage authentication process that requires a first stage of inputting a valid password and a second stage of performing a hardware authentication process using a hardware device issued by an emergency services agency. The authentication process may include receiving input from a hardware device issued to the emergency services provider by an emergency services agency to enable authentication of the emergency services provider to the electronic device of the patient that is configured to aggregate electronic medical records associated with the patient, and determining a status of the emergency services provider based on the received input from the hardware device. The authentication process also may include receiving, from the emergency services provider, input indicating a user identifier and a password associated the emergency services provider, and determining a status of the emergency services provider based on the user identifier and the password.

In some implementations, the patient electronic device may determine whether the emergency services provider is licensed or may determine a credential level of the emergency services provider 920. The credential level may be at least one of ambulance personnel, an emergency room doctor, and a surgeon that performs emergency surgery.

In some examples, the authentication process may be performed without receiving input from the patient. In other examples, authentication of the emergency services provider may be conditioned on receiving a biometric input from the patient indicating that the patient is physically near the electronic device of the patient. The biometric input may be a fingerprint scan or retinal scan that the patient may be able to provide even when the patient is unconscious.

The patient electronic device 930 accesses, from electronic storage, preferences of the patient 910 regarding emergency services provider access to medical records of the patient (1030). The patient electronic device 930 may access profile information from electronic storage of the patient electronic device 930 or may access, over a network, profile information from electronic storage of a device remote from the patient electronic device 930. The profile information may indicate preferences of the patient in providing electronic medical records to emergency service providers.

The patient electronic device 930 determines a level of access to the medical records associated with the patient 910 to provide to the emergency services provider 920 based on the determined status of the emergency services provider 920 and the accessed preferences of the patient (1040). The patient electronic device 930 may determine the level of access from among at least three levels of access. The three levels of access may include a full access level that enables full access to all medical records for the patient, a no access level that does not enable any access to medical records for the patient, and an intermediate access level that enables access that is between the full access level and the no access level. In one example, the patient electronic device 930 may determine to provide access to at least some of the medical records associated with the patient in response to determining that the emergency services provider is licensed, and may determine not to provide any access to the medical records associated with the patient in response to determining that the emergency services provider is not licensed. In another example, the patient electronic device 930 may determine to provide a first level of access to the emergency services provider 920 in response to determining that the emergency services provider 920 is ambulance personnel, the patient electronic device 930 may determine to provide a second level of access to the emergency services provider 920 in response to determining that the emergency services provider 920 is an emergency room doctor, and the patient electronic device 930 may determine to provide a third level of access to the emergency services provider in response to determining that the emergency services provider is a surgeon that performs emergency surgery. The third level of access may be different than the first level of access and the second level of access.

The patient electronic device 930 aggregates electronic medical records associated with the patient 910 based on the determined level of access to provide to the emergency services provider 920 (1050). The patient electronic device 930 aggregates electronic medical records associated with the patient 910 using techniques described above. The type and extent of electronic medical records aggregated may be controlled by the determined level of access to provide to the emergency services provider 920. The patient electronic device 930 may automatically aggregate electronic medical records without further input from the emergency services provider 920.

The patient electronic device 930 enables display, to the emergency services provider 920, of the aggregated electronic medical records associated with the patient 910 (1060). The patient electronic device 930 may display a virtual assemblage of the electronic medical records as a single file. The electronic device 930 also may perform statistical processing or grouping on the received electronic medical records prior to displaying electronic medical record information. The electronic device 930 further may transmit the electronic medical record information to another device and the other device may display the electronic medical record information. Transmitting the electronic medical record information to another device for display may be beneficial when the other device has a larger or otherwise more suited display for viewing electronic medical records and/or any images (e.g., x-rays) associated with the electronic medical records.

Figure 11:
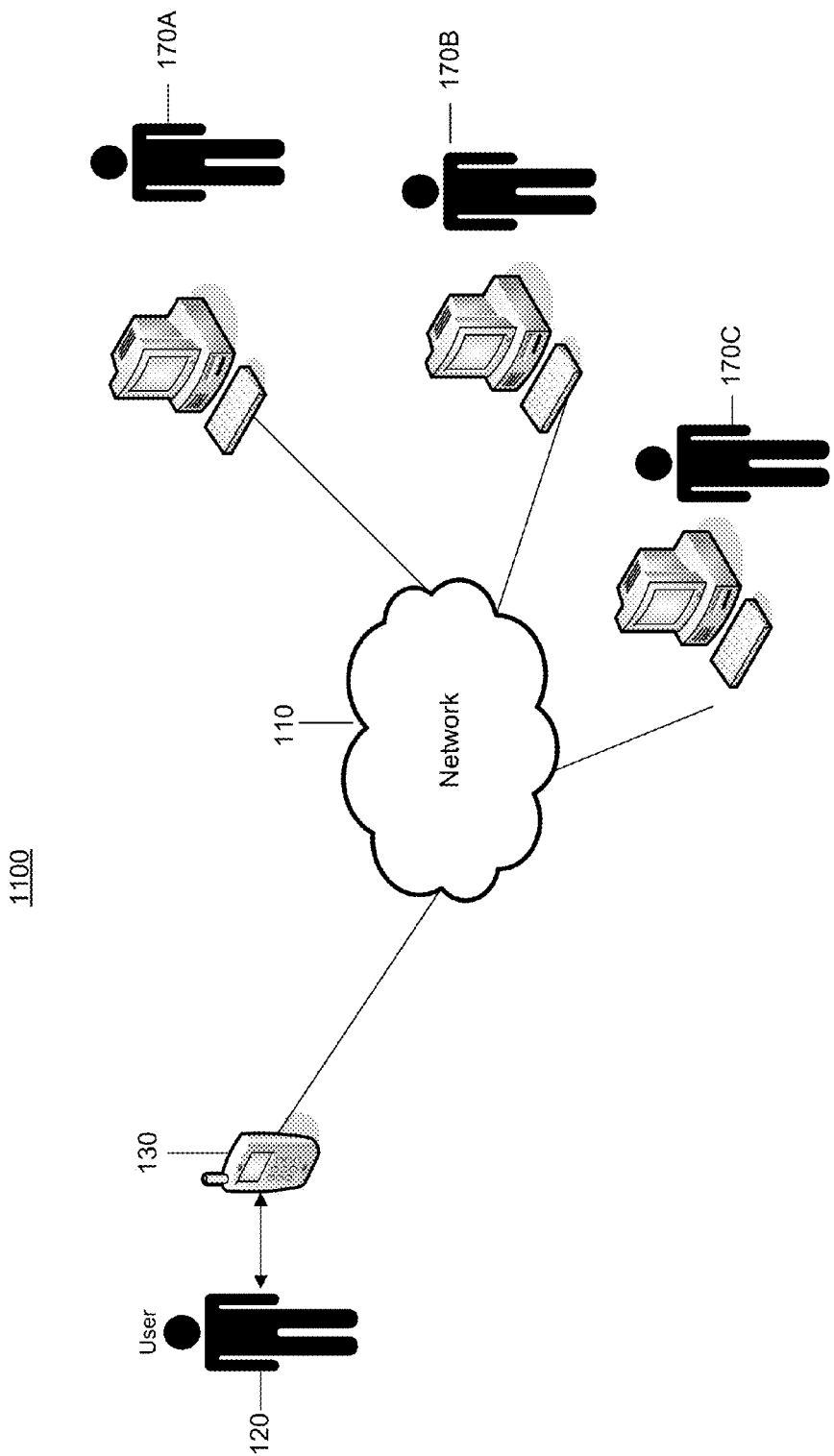
FIG. 11 shows an example system 1100 for a user to solicit bids for healthcare service.

In some implementations, a patient 120 may anonymously broadcast a request for medical services to a community of healthcare professionals subscribing to the broadcasting channel, as illustrated in FIG. 11. The broadcasting channel may include any form of electronic communication, for example, email, SMS. As illustrated, the broadcast request may be sent by an application program on user electronic device 130. The application program may be configured to mask any information identifying the submitting patient. In one example, the application program may be configured to abstract the identifying information into classification parameters based on, for example, gender and age group. However, the broadcast request may include a specific level of information of the patient, for example, the general symptoms, the specialty that may be relevant. Generally, the patient may configure the granularity of information to be shared. For common symptoms, a default or template setting may be applied regarding the amount and abstractness of patient information to be shared. For more special conditions, the level of information may be more specific to the target organ or system. For example, if the symptom includes angina, the information may include cardiac parameters such as blood pressure, low density cholesterol (LDL) levels, or high-density cholesterol (HDL) level. In this example, the level of information may not include information identifying the patient.

Healthcare professionals 170A to 170C may review the request submitted and determine if they are capable of offering assistance, if they have the capacity to provide the requested service, and if they cooperate with the patient's health insurance policy. Healthcare professionals 170A to 170C may additionally provide estimate of fees, available time for office visits, and services available at the office, to the requesting user 120. The response may be in the form of bid, may further include credential information of the healthcare professional, including, for example, number of years in practice, graduating school, board certifications, patient review statistics and testimonials from sample patients.

Figure 12:
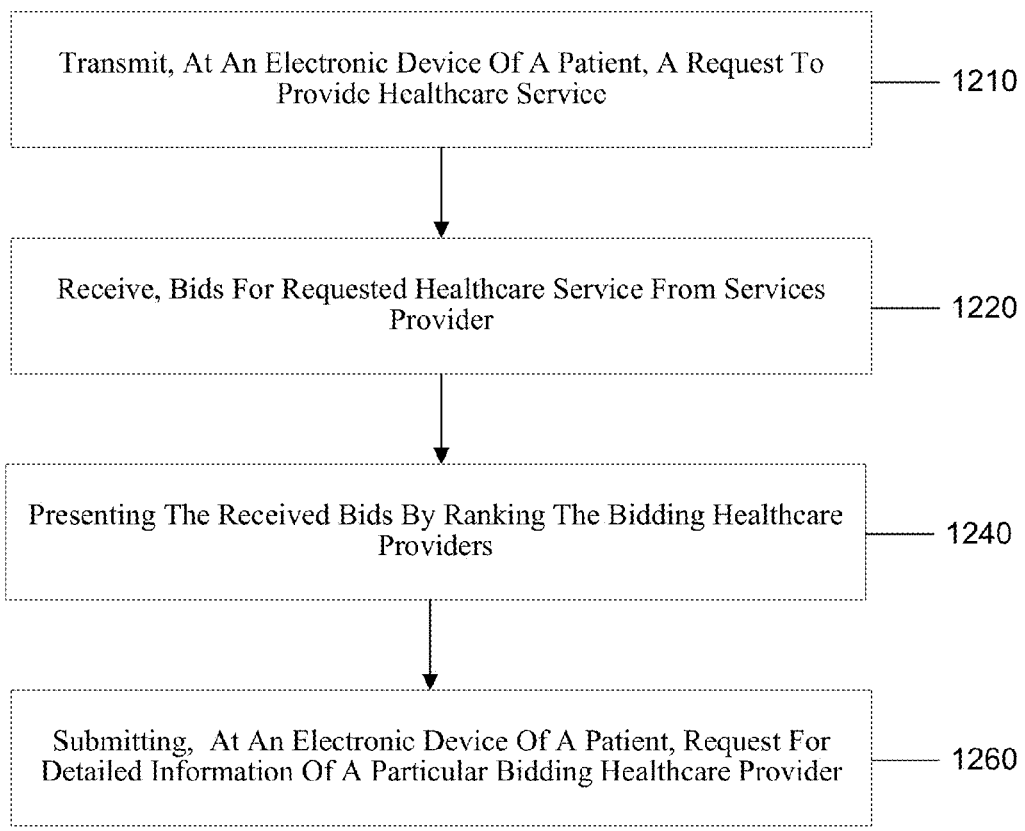
FIG. 12 is a flow chart showing the process for a user to solicit bids for healthcare service.

Referring to the flow chart 1200 of FIG. 12, user 120 may submit, from an application program at electronic device 130, a request to provide healthcare service for a particular condition (1210). The bids may be collected from network 110 by the application program on user electronic device 130 (1220). The bids may be presented to a requesting user through an informative interface on user electronic device 130 (1240). In some instances, the application program may rank the received bids. In one example, the ranking may be according to the degree of match between an interest of the healthcare provider and the requested healthcare service.

In another example, the ranking may be based on the price estimate provided by the bidding healthcare provider of the requested healthcare service. In this example, the requesting user 120 may configure the ranking as in ascending order or descending order. In this example, the requesting user 120 may fine tune the ranking based on an adjustment factor that takes into account of, for example, historical price adjustments by the healthcare providers at the time of billing. In some instances, the historical price adjustment may include an average upward or downward adjustment amount at the time of billing. In other instances, reported historical price disputes between the healthcare provider and the health insurance carrier of the patient may be flagged for the requesting patient 120. Details of such reports may become available to the health insurance carrier of the patient, for example, upon request by the health insurance carrier.

In yet another example, the ranking may be based on the background experience of the bidding healthcare professional. The background experience of the bidding healthcare professional may include the area of specialization of the bidding healthcare professional. For instance, the application program on user electronic device 130 may apply more weight toward the more recent experience of the bidding health care provider in the area of specialization. Such tapering may emphasize the freshness of the relevant experience that the bidding healthcare provider may have. In another instance, the application program on user electronic device 130 may apply more weight toward the bidding health care provider if he or she has worked with known opinion leaders in the area of specialization.

In still another example, the ranking may be based on the availability of the bidding healthcare providers. In one instance, the ranking may be in the order of the next immediately open appointment. In this instance, the ranking may additionally factor in the distance from the requesting user to the facility of each bidding healthcare provider.

In yet still another example, the ranking may be based on the safety record of the bidding healthcare providers within a particular healthcare network of a carrier. In one illustration, the safety record may include number of post-procedure complications reported to the health insurance carrier regarding a procedure performed by the healthcare provider in providing the requested service. In a similar illustration, the safety record of the bidding healthcare providers may factor in medical malpractice lawsuits filed against the bidding healthcare providers, especially when such malpractice lawsuits have reached final adjudication.

In another additional example, the ranking may be based on the number of patients treated by the bidding healthcare providers within a particular healthcare network. By way of illustration, the application program may rank the bidding healthcare providers according to the number of procedures performed by each bidder in the past, for example, three years, when providing the requested service.

When the bids are received, they may be presented to the patient, for example, in a ranked order as described above. The patient may use his or her own prerogative to select a bid based on the patient's needs. Before making a selection of a bid, the patient may request more detailed information of a particular bidding healthcare provider. Such detailed information may include, for example, malpractice lawsuits, if any, filed against the particular healthcare provider; disciplinary actions by a board against the particular healthcare provider; references that the particular healthcare provider has provided; media coverage of the particular healthcare provider; peer review of the particular healthcare provider. The request for more detailed information may be submitted by the patient at electronic device 130 of the patient (1260).

Figure 13:
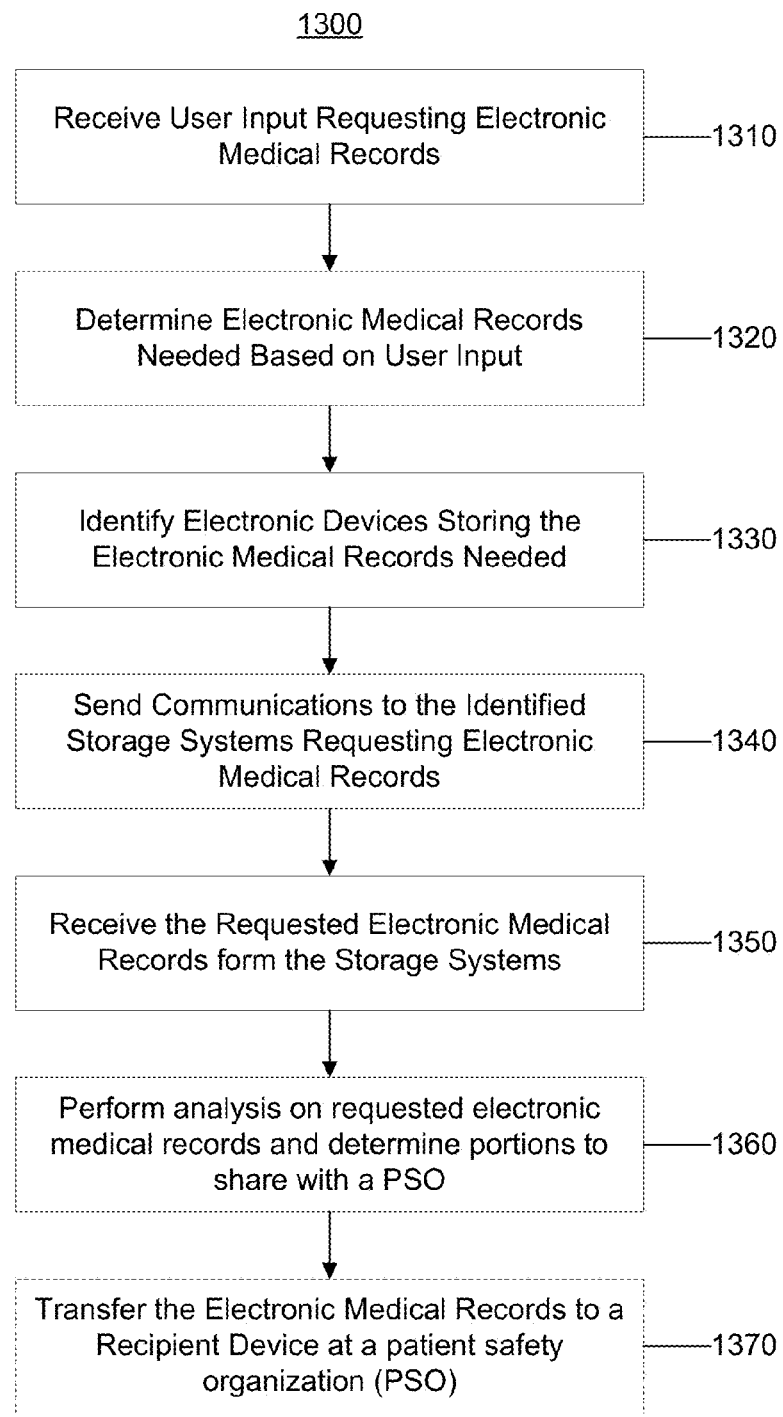
FIG. 13 is another flow chart of a process for accessing electronic medical records to share with a Patient Safety Organization (PSO).

FIG. 13 is a flow chart of a process 1300 for accessing and presenting electronic medical records in the context of interacting with a PSO. For convenience, particular components described with respect to FIG. 1A are referenced as performing the process 1300. However, similar methodologies may be applied in other implementations where different components are used to define the structure of the system, or where the functionality is distributed differently among the components shown by FIG. 1A.

The user electronic device 130 receives user input requesting electronic medical records (1310). As described with respect to FIG. 3, in one example, the user 120 may supply user input (e.g., using a keyboard, keypad, mouse, stylus, etc.) to the user electronic device 130 to initiate a request for electronic medical records. In other examples, the recipient 170 may enter user input to the user electronic device 130 or the user electronic device 130 may receive user input over connection 190 or network 110 from, for instance, the recipient electronic device 180.

The user electronic device 130 determines the electronic medical records needed based on the user input (1320). For example, the user electronic device 130 determines whether the request for records is a request for all electronic medical records associated with the user 120 or whether only a subset of electronic medical records is needed. For example, the user electronic device 130 determines whether the request is for electronic medical records related to orthopedic and muscular treatment. For example, the user electronic device 130 determines whether the request is for electronic medical records from a particular doctor and a particular hospital. For example, the user electronic device 130 determines whether the request is for electronic medical records within the last ten years. Other restrictions may be placed by the user 120 on a records request.

The user electronic device 130 determines the location of the electronic medical records needed (1330). For example, the user electronic device 130 may determine whether the user electronic device 130 stores the requested records locally on the user electronic device 130 or whether an electronic device at a remote location stores the requested records. When the requested records, or portions thereof, are stored remotely in distributed storage, user electronic device 130 may determine the location of storage by the address information of each portion. As noted above with respect to FIG. 3, the address information may include a URL, a stub, a hyperlink, or any other exemplary location direct or indirect mechanism.

After determining the location of the records needed, the user electronic device 130 sends communications requesting records to electronic devices storing the requested records (1340). For example, the user electronic device 130 may send electronic communications over network 110 to the multiple record storage systems 140, 150, and 160 requesting records. As noted above with respect to FIG. 3, the electronic communication may identify the user 120 requesting the records, the user electronic device 130 requesting the records, the recipient 170, the recipient electronic device 180 that may receive the records, the records that are requested and/or the restrictions placed on the records request. In this particular illustration, a PSO may be an example recipient 170. A data server at the PSO may be an example recipient electronic device 180.

The user electronic device 130 receives records sent from electronic devices storing the requested records in response to receiving a communication requesting records (1350). For example, the user electronic device 130 may receive electronic records over network 110 from the multiple record storage systems 140, 150, and 160. The user electronic device 130 may transmit acknowledgements to the record storage system sending the electronic medical records when the user electronic device 130 receives the electronic medical records.

The user electronic device 130 performs analysis on the requested electronic medical records and determines portions to share with a PSO (1360). In some implementations, a healthcare provider, such as a hospital, a treating physician, or a pharmacist, may submit anonymized electronic medical records of a patient to a PSO. The submission may be pursuant to a contractual agreement between the healthcare provider and the PSO. In some implementations, patient 120 may enter into an agreement with a healthcare provider holding the electronic medical record of patient 120. In the above context, the user electronic device 130 may analyze the electronic medical records received from distributed storage. The analysis may be conducted pursuant to the agreement with the healthcare provider and PSO so that sensitive information, patient-identifying information, or stigmatic information may be purged from the received electronic medical records. In some examples, the agreement may place further restrictions on the portions of the received electronic medical records that may be shared with, for example, the PSO.

The user electronic device 130 may, optionally, transfer the records to the recipient electronic device 180 (1370) at a PSO. The transfer may be pursuant to the agreement and only permissible portions under the agreement may be transmitted without patient-identifying information to the PSO. As described herein, the PSO, or a group of PSOs, may perform analysis on the aggregated electronic medical records. The summary information generated by the analysis may be transferred to, for example, healthcare providers who have contributed in submitting anonymized electronic medical records.

The described systems, methods, and techniques may be implemented in digital electronic circuitry, computer hardware, firmware, software, or in combinations of these elements. Apparatus embodying these techniques may include appropriate input and output devices, a computer processor, and a computer program product tangibly embodied in a machine-readable storage device for execution by a programmable processor. A process embodying these techniques may be performed by a programmable processor executing a program of instructions to perform desired functions by operating on input data and generating appropriate output. The techniques may be implemented in one or more computer programs that are executable on a programmable system including at least one programmable processor coupled to receive data and instructions from, and to transmit data and instructions to, a data storage system, at least one input device, and at least one output device. Each computer program may be implemented in a high-level procedural or object-oriented programming language, or in assembly or machine language if desired; and in any case, the language may be a compiled or interpreted language. Suitable processors include, by way of example, both general and special purpose microprocessors. Generally, a processor will receive instructions and data from a read-only memory and/or a random access memory. Storage devices suitable for tangibly embodying computer program instructions and data include all forms of non-volatile memory, including by way of example semiconductor memory devices, such as Erasable Programmable Read-Only Memory (EPROM), Electrically Erasable Programmable Read-Only Memory (EEPROM), and flash memory devices; magnetic disks such as internal hard disks and removable disks; magneto-optical disks; and Compact Disc Read-Only Memory (CD-ROM). Any of the foregoing may be supplemented by, or incorporated in, specially-designed ASICs (application-specific integrated circuits).

In one implementation, a brokering application is sent to the mobile device using a mobile device message (e.g., a specially-configured MMS ("Multimedia Messaging Service") or SMS ("Short message Service") message) configured to load an application. For example, a MMS message may be sent to a mobile device. The MMS message may include a URL ("Uniform Resource Locator") to an installation application. The user may retrieve the URL in order to install a brokering application. The URL may include a link to a configured to install a BREW ("Binary Runtime Environment for Wireless") or J2ME ("Binary Runtime Environment for Wireless") program that acts as the brokering application.

A user may contact their insurance provider, a medical records provider, or a health care provider in order to receive the program. Thus, a user may enter their address information (e.g., phone number or email address) on a web site (or through a call center). The insurance provider then may respond with a link to an installation program. The user selects the link to install a brokering application onto a wireless phone, and then enters user information (e.g., authentication and identification information) with the brokering application. Once authenticated, a record storage system then may provide address information for the user's records. The record storage system may transmit secure URLs to the brokering application. The brokering application then can be configured to store the URLs, and access records across the URLs.

As a user interacts with different record storage systems, the user may transmit identification information for each of the different record storage providers so that the brokering application can be configured to add address information for each of the record storage providers. For example, a user visiting a medical test center may provide a wireless telephone number to access test results. The medical test center then may send a message to enroll the user's mobile device into the network of devices permitted to access records securely published by the medical test center. Once the user has successfully completed the validation regimen, address information for the user's tests may be added to a list of URLs administered by the brokering application. In one configuration, the brokering application is configured to store address information for insurance and claims processing, primary and specialist physicians, and pharmacy services. By configuring the brokering application on the mobile device to store address information for securely published medical records, the user may use their mobile device to selectively distribute records to interested parties, such as a health care provider.

To illustrate, a user visiting their physician may register with a physician's "front desk." The front desk may include a Bluetooth™ transceiver configured to prompt a brokering application for the user's medical records, test results, and insurance information. The user receives a message from the brokering application indicating that the physician's front desk is requesting access to the medical records, test results, and insurance information. The user then may "accept" the prompt to instruct the brokering application to access requested records. The brokering application then accesses URLs for each of the requested records from each of the record storage providers. The brokering application then may present authentication information, or rely on previously-provided authentication information. The record storage providers may provide PDF (Portable Document Format) files with the requested information.

The mobile device receives the requested records and transmits the records to the physician's front desk. The front desk system then may distribute records to the necessary physicians, nurses, and claims processing personnel. The user then may receive medical services. Depending on the communications protocol used, the mobile device may either maintain communications with the front desk system (using, for example, Wi-Fi wireless LAN technologies) or disconnect from the front desk system (using, for example, Bluetooth™ technologies).

As a result of the user receiving services, and a physician updating medical records, requesting tests, and writing a prescription, the health care provider may wish to update the user's records. The brokering application then may receive communications from the front desk system (or other systems in the physician's office) and request to transmit the information to the respective record storage providers. The user then may acknowledge the prompt to permit the mobile device to receive the updated medical records, testing requests, and prescriptions. The brokering application on the mobile device then may retrieve address information for each of the records, and transmit the updated information to each of the medical storage providers. Alternatively, the front desk system then may transmit each of the updates to email addresses associated with the user, where the updated information is processed and sent to each of the respective medical service providers. Such a configuration may be employed where access to the information is deemed especially sensitive and updates to the information deemed less of a concern since the updating system already has access to the information being updated.

In one implementation, specialized units and systems, such as emergency room and ambulatory personnel and systems may be provided with special privileges to access a record storage provider. For example, in the event that a patient is unable to access or interface with a mobile device to provide medical records, perhaps because the patient is unconscious or is in a diminished capacity, the mobile device may be configured to enable accredited personnel and systems to access required records. In one configuration, the mobile device challenges personnel to enter accredited access information for the emergency room. Alternatively or in addition, the mobile device may be configured to read MAC ("Media Access Control") address information from local wireless systems. The mobile device then may be configured to read the MAC address from an emergency room system, and transmit the MAC address for the emergency room system to a validation system (e.g., a security program operated by a record storage provider). The validation system then may determine if the MAC address is found among the list of accredited MAC addresses for emergency room systems. The mobile device may be configured to automatically validate MAC addresses without intervention to reduce the burden on emergency room personnel. In still another configuration, the MAC address filtering is used in addition to requiring emergency room personnel to enter a PIN ("Personal Identifier Number") for the specific emergency room where the patient is being seen.

In one configuration, in response to determining that emergency services personnel are accessing a medical record, the storage record provider may be configured to transmit a DNR ("Do Not Resuscitate") message to the emergency services personnel. For example, the mobile device may be configured to generate a noticeable display and/or require an acknowledgement of the patient's DNR status. The record storage provider also may be configured to transmit a voice and electronic mail message contacting the emergency services personnel with the DNR status information.

A pharmacy also may be enrolled in a list of registered pharmacies permitted to access a patient's pharmacological record. For example, a pharmacy may use a specialized printer with a short range wireless transmitter configured to automatically interrogate brokering applications on mobile devices. In response to entering a pharmacy, the specialized printer may automatically interrogate the brokering application for prescription information. The brokering application may communicate with a pharmacy record provider to determine if the specialized printer is associated with an accredited pharmacy. As a result of recognizing the specialized printer as being associated with an accredited pharmacy, the specialized printer accesses electronic records with unfilled and/or refill prescriptions and prints out the prescription. The pharmacist then may fulfill the prescription.

It will be understood that various modifications may be made without departing from the spirit and scope. For example, advantageous results still could be achieved if steps of the disclosed techniques were performed in a different order and/or if components in the disclosed systems were combined in a different manner and/or replaced or supplemented by other components. Other implementations are within the scope of the description.

What is claimed is:

1. A method of using a wireless device that has a medical record application to aggregate electronic medical records associated with a user, and then to transmit the aggregated electronic medical records to a medical provider record system that is configured to use the wireless device as a source for the aggregated electronic medical records, the method comprising:

transmitting, from the wireless device to a first communication device, a first request for a first electronic medical record associated with the user and stored in electronic storage accessible by the first communication device, the first request including first authentication information;

transmitting, from the wireless device to a second communication device different than the first communication device, a second request for a second electronic medical record associated with the user and stored in electronic storage accessible by the second communication device, the second request including second authentication information;

receiving, at the wireless device from the first communication device, the first electronic medical record in response to the first communication device receiving the first request and authenticating the first request based on the first authentication information;

confirming, at the wireless device, 1) an identity of the first communication device, and 2) authenticity of the first electronic medical record received from the first communication device based at least on comparing third authentication information received from the first communication device with data accessible by the wireless device that corresponds to the third authentication information;

receiving, at the wireless device from the second communication device, the second electronic medical record in response to the second communication device receiving the second request and authenticating the second request based on the second authentication information so as to thereby aggregate the first and second medical records at the wireless device;

confirming, at the wireless device, 1) an identity of the second communication device, and 2) authenticity of the second electronic medical record received from the second communication device based at least on comparing fourth authentication information received from the second communication device with data accessible by the wireless device that corresponds to the fourth authentication information;

establishing a secure, authenticated connection between the wireless device and the medical provider record system in response to the wireless device having authenticated fifth authentication information received from the medical provider record system by comparing the fifth authentication information received from the medical provider record system with data accessible by the wireless device that corresponds to the fifth authentication information; and transmitting, from the wireless device, the first and second electronic medical records to the medical provider record system using the secure, authenticated connection.

2. The method of claim 1, further comprising configuring the first communication device to deny the first request in response to the first communication device failing to receive the first authentication information, and configuring, and configuring the second communication device to deny the second request in response to the second communication device failing to receive the second authentication information.

3. The method of claim 1, wherein at least one of the first, second, third, fourth, and fifth authentication information is an electronic signature.

4. The method of claim 1, wherein at least one of the third, fourth, and fifth authentication information is a digital certificate.

5. The method of claim 1, wherein at least one of the third and fourth authentication information is an electronic postmark.

6. The method of claim 1, further comprising:
assembling the first and second electronic medical records; and
enabling display of the assembled first and second electronic medical records at the medical provider record system using the secure, authenticated connection.

7. The method of claim 1, wherein the wireless device and the medical provider record system constitute separate devices, and further comprising:
assembling the first and second electronic medical records; and
enabling display of the assembled first and second electronic medical records at the wireless device.

8. The method of claim 1, further comprising accessing filter criteria associated with a service to be provided for the user, wherein the first and second requests include the filter criteria, and the first and second medical records received at the wireless device meet the filter criteria.

9. The method of claim 1, wherein confirming authenticity of the first electronic medical record comprises confirming that the first electronic medical record has not been altered subsequent to transmission of the first electronic medical record by the first communication device, and wherein confirming authenticity of the second electronic medical record comprises confirming that the second electronic medical record has not been altered subsequent to transmission of the second electronic medical record by the second communication device.

10. The method of claim 9, wherein confirming authenticity of the first electronic medical record and confirming authenticity of the second electronic medical record includes use of at least one of: a digital certificate, an electronic postmark, a hash code, and a watermark.

11. The method of claim 1, wherein the wireless device is at least one of a server and a personal computer.

12. The method of claim 1, wherein the medical provider record system is associated with a pharmacy, and at least one of the first and second electronic medical records includes prescription information, the method further comprising:

receiving, at the wireless device, a third request for the medical record application to deliver the prescription information upon the wireless device being disposed proximate the pharmacy.

13. The method of claim 12, further comprising enabling transmission and printing of the prescription information included in the at least one of the first and second electronic medical records at the pharmacy upon receipt, by the wireless device, of the third request for the medical record application to deliver the prescription information.

14. The method of claim 1, wherein establishing a secure, authenticated connection between the wireless device and the medical provider record system comprises establishing a secure, authenticated connection between the wireless device and the medical provider record system over the Internet.

15. The method of claim 1, further comprising:
determining at least one of a summary and a statistical analysis of the first and second electronic medical records; and
enabling display of the at least one of the summary and the statistical analysis of the first and second electronic medical records.

16. The method of claim 1, wherein each of the first and second electronic medical records constitute a partial electronic medical record, the method further comprising:
assembling the first and second electronic medical records to generate a complete electronic medical record.

17. The method of claim 1, further comprising:
receiving, at the wireless device, (i) a request to add an electronic medical record, and (ii) information associated with the electronic medical record to be added; and
generating, by the wireless device and based on the request to add the electronic medical record, an electronic medical record that includes at least a portion of the information associated with the medical record to be added.

18. The method of claim 1, wherein the first request is transmitted from the wireless device to the first communication device through a server and the second request is transmitted from the wireless device to the second communication device through the server.

19. The method of claim 1, wherein the at least one of the first electronic medical record and the second electronic medical record is associated with one or more use restrictions.

20. The method of claim 19, wherein the one or more use restrictions include a restriction indicating that at least one of the first electronic medical record and the second electronic medical record expires after a period of time, such that the at least one of the first electronic medical record and the second electronic medical record is no longer accessible after the period of time.

21. The method of claim 19, wherein the one or more use restrictions include a restriction indicating that at least one of the first electronic medical record and the second electronic medical record cannot be printed.

22. The method of claim 1, further comprising transmitting, from the wireless device, the first and second electronic medical records to one or more other medical provider record systems.

23. The method of claim 22, further comprising:
transmitting, from the wireless device, a request for a bid to at least one of the medical provider record systems;
receiving, at the wireless device, a bid from at least one of the medical provider record systems; and ranking, by the wireless device, the received bids based on at least one of price, background experience, availability, safety record, and number of patients.

24. An apparatus for using a wireless device that has a medical record application to aggregate electronic medical records associated with a user, and then to transmit the aggregated electronic medical records to a medical provider record system that is configured to use the wireless device as a source for the aggregated electronic medical records, the apparatus comprising:

means for transmitting, from the wireless device to a first communication device, a first request for a first electronic medical record associated with the user and stored in electronic storage accessible by the first communication device, the first request including first authentication information;

means for transmitting, from the wireless device to a second communication device different than the first communication device, a second request for a second electronic medical record associated with the user and stored in electronic storage accessible by the second communication device, the second request including second authentication information;

means for receiving, at the wireless device from the first communication device, the first electronic medical record in response to the first communication device receiving the first request and authenticating the first request based on the first authentication information;

means for confirming, at the wireless device, 1) an identity of the first communication device, and 2) authenticity of the first electronic medical record received from the first communication device based at least on comparing third authentication information received from the first communication device with data accessible by the wireless device that corresponds to the third authentication information;

means for receiving, at the wireless device from the second communication device, the second electronic medical record in response to the second communication device receiving the second request and authenticating the second request based on the second authentication information so as to thereby aggregate the first and second medical records at the wireless device;

means for confirming, at the wireless device, 1) an identity of the second communication device, and 2) authenticity of the second electronic medical record received from the second communication device based at least on comparing fourth authentication information received from the second communication device with data accessible by the wireless device that corresponds to the fourth authentication information;

means for establishing a secure, authenticated connection between the wireless device and the medical provider record system in response to the wireless device having authenticated fifth authentication information received from the medical provider record system by comparing the fifth authentication information received from the medical provider record system with data accessible by the wireless device that corresponds to the fifth authentication information; and means for transmitting, from the wireless device, the first and second electronic medical records to the medical provider record system using the secure, authenticated connection.

25. A non-transitory computer-readable storage medium encoded with a computer program for using a wireless device that has a medical record application to aggregate electronic medical records associated with a user, and then to transmit the aggregated electronic medical records to a medical provider record system that is configured to use the wireless device as a source for the aggregated electronic medical records, the computer program being executed by a processor to perform operations comprising:

transmitting, from the wireless device to a first communication device, a first request for a first electronic medical record associated with the user and stored in electronic storage accessible by the first communication device, the first request including first authentication information;

transmitting, from the wireless device to a second communication device different than the first communication device, a second request for a second electronic medical record associated with the user and stored in electronic storage accessible by the second communication device, the second request including second authentication information;

receiving, at the wireless device from the first communication device, the first electronic medical record in response to the first communication device receiving the first request and authenticating the first request based on the first authentication information;

confirming, at the wireless device, 1) an identity of the first communication device, and 2) authenticity of the first electronic medical record received from the first communication device based at least on comparing third authentication information received from the first communication device with data accessible by the wireless device that corresponds to the third authentication information;

receiving, at the wireless device from the second communication device, the second electronic medical record in response to the second communication device receiving the second request and authenticating the second request based on the second authentication information so as to thereby aggregate the first and second medical records at the wireless device;

confirming, at the wireless device, 1) an identity of the second communication device, and 2) authenticity of the second electronic medical record received from the second communication device based at least on comparing fourth authentication information received from the second communication device with data accessible by the wireless device that corresponds to the fourth authentication information;

establishing a secure, authenticated connection between the wireless device and the medical provider record system in response to the wireless device having authenticated fifth authentication information received from the medical provider record system by comparing the fifth authentication information received from the medical provider record system with data accessible by the wireless device that corresponds to the fifth authentication information; and transmitting, from the wireless device, the first and second electronic medical records to the medical provider record system using the secure, authenticated connection.

26. The computer-readable storage medium of claim 25, further comprising configuring the first communication device to deny the first request in response to the first communication device failing to receive the first authentication information, and configuring, and configuring the second communication device to deny the second request in response to the second communication device failing to receive the second authentication information.

27. The computer-readable storage medium of claim 25, wherein at least one of the first, second, third, fourth, and fifth authentication information is an electronic signature.

28. The computer-readable storage medium of claim 25, wherein at least one of the third, fourth, and fifth authentication information is a digital certificate.

29. The computer-readable storage medium of claim 25, wherein at least one of the third and fourth authentication information is an electronic postmark.

30. The computer-readable storage medium of claim 25, the operations further comprising:
    assembling the first and second electronic medical records; and
    enabling display of the assembled first and second electronic medical records at the medical provider record system using the secure, authenticated connection.

31. The computer-readable storage medium of claim 25, wherein the wireless device and the medical provider record system constitute separate devices, and the operations further comprising:
    assembling the first and second electronic medical records; and
    enabling display of the assembled first and second electronic medical records at the wireless device.

32. The computer-readable storage medium of claim 25, further comprising accessing filter criteria associated with a service to be provided for the user, wherein the first and second requests include the filter criteria, and the first and second medical records received at the wireless device meet the filter criteria.

33. The computer-readable storage medium of claim 25, wherein confirming authenticity of the first electronic medical record comprises confirming that the first electronic medical record has not been altered subsequent to transmission of the first electronic medical record by the first communication device, and wherein confirming authenticity of the second electronic medical record comprises confirming that the second electronic medical record has not been altered subsequent to transmission of the second electronic medical record by the second communication device.

34. The computer-readable storage medium of claim 33, wherein confirming authenticity of the first electronic medical record and confirming authenticity of the second electronic medical record includes use of at least one of: a digital certificate, an electronic postmark, a hash code, and a watermark.

35. The computer-readable storage medium of claim 25, wherein the wireless device is at least one of a server and a personal computer.

36. The computer-readable storage medium of claim 25, wherein the medical provider record system is associated with a pharmacy, and at least one of the first and second electronic medical records includes prescription information, the operations further comprising:
    receiving, at the wireless device, a third request for the medical record application to deliver the prescription information upon the wireless device being disposed proximate the pharmacy.

37. The computer-readable storage medium of claim 36, further comprising enabling transmission and printing of the prescription information included in the at least one of the first and second electronic medical records at the pharmacy upon receipt, by the wireless device, of the third request for the medical record application to deliver the prescription information.

38. The computer-readable storage medium of claim 25, wherein establishing a secure, authenticated connection between the wireless device and the medical provider record system comprises establishing a secure, authenticated connection between the wireless device and the medical provider record system over the Internet.

39. The computer-readable storage medium of claim 25, the operations further comprising:
    determining at least one of a summary and a statistical analysis of the first and second electronic medical records; and
    enabling display of the at least one of the summary and the statistical analysis of the first and second electronic medical records.

40. The computer-readable storage medium of claim 25, wherein each of the first and second electronic medical records constitute a partial electronic medical record, the operations further comprising:
    assembling the first and second electronic medical records to generate a complete electronic medical record.

41. The computer-readable storage medium of claim 25, the operations further comprising:
    receiving, at the wireless device, (i) a request to add an electronic medical record, and (ii) information associated with the electronic medical record to be added; and
    generating, by the wireless device and based on the request to add the electronic medical record, an electronic medical record that includes at least a portion of the information associated with the medical record to be added.

42. The computer-readable storage medium of claim 25, wherein the first request is transmitted from the wireless device to the first communication device through a server and the second request is transmitted from the wireless device to the second communication device through the server.

43. The computer-readable storage medium of claim 25, wherein the at least one of the first electronic medical record and the second electronic medical record is associated with one or more use restrictions.

44. The computer-readable storage medium of claim 43, wherein the one or more use restrictions include a restriction indicating that at least one of the first electronic medical record and the second electronic medical record expires after a period of time, such that the at least one of the first electronic medical record and the second electronic medical record is no longer accessible after the period of time.

45. The computer-readable storage medium of claim 43, wherein the one or more use restrictions include a restriction indicating that at least one of the first electronic medical record and the second electronic medical record cannot be printed.

46. The computer-readable storage medium of claim 25, the operations further comprising transmitting, from the wireless device, the first and second electronic medical records to one or more other medical provider record systems.

47. The computer-readable storage medium of claim 46, the operations further comprising:
    transmitting, from the wireless device, a request for a bid to at least one of the medical provider record systems;
    receiving, at the wireless device, a bid from at least one of the medical provider record systems; and
    ranking, by the wireless device, the received bids based on at least one of price, background experience, availability, safety record, and number of patients.

* * * * *